US012788919B2

(12) United States Patent
Yu et al.

(10) Patent No.: US 12,788,919 B2
(45) Date of Patent: Nov. 10, 2026

(54) BITE BLOCK AND ASSEMBLIES INCLUDING SAME

(71) Applicant: Masimo Corporation, Irvine, CA (US)

(72) Inventors: Edmond Wing Lun Yu, Chino Hills, CA (US); Mahdi Mohammadi, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 996 days.

(21) Appl. No.: 17/937,746

(22) Filed: Oct. 3, 2022

(65) Prior Publication Data

US 2023/0111198 A1 Apr. 13, 2023

Related U.S. Application Data

(60) Provisional application No. 63/262,235, filed on Oct. 7, 2021.

(51) Int. Cl.

*A61M 16/04* (2006.01)
*A61M 16/06* (2006.01)
*A61M 16/12* (2006.01)

(52) U.S. Cl.

CPC .... *A61M 16/0493* (2014.02); *A61M 16/0666* (2013.01); *A61M 16/12* (2013.01)

(58) Field of Classification Search

None

See application file for complete search history.

(56) References Cited

U.S. PATENT DOCUMENTS 718,785 A 1/1903 McNary
1,873,160 A 8/1932 Sturtevant
2,470,297 A 5/1949 Fields
3,490,452 A 1/1970 Greenfield
3,508,543 A 4/1970 Aulicono
(Continued)

FOREIGN PATENT DOCUMENTS

CN 306848977 9/2021
DE 1 113 065 8/1961
(Continued)

OTHER PUBLICATIONS

US 2022/0192529 A1, 06/2022, Al-Ali et al. (withdrawn)
(Continued)

*Primary Examiner* — Valerie L Woodward

(74) *Attorney, Agent, or Firm* — Knobbe, Martens, Olson & Bear, LLP

(57) ABSTRACT

A bite block includes a main body and a mouthpiece extending outward from the main body and configured to be positioned in a mouth of the subject when the bite block is in use. The mouthpiece can include a main channel configured to receive an endoscopic tube and a sampling channel configured to receive orally exhaled gases from the subject. The bite block can include a gas delivery channel configured to direct gases into the subject's mouth, the gas delivery channel extending through a portion of the main body and through a portion of the main channel such that the gas delivery channel is in fluid communication with the main channel. The bite block can include a recess extending along a portion of the first surface of the main body proximate the gas delivery channel and configured to receive a portion of a gas delivery tube.

20 Claims, 21 Drawing Sheets

(56) References Cited

U.S. PATENT DOCUMENTS

| | | | |
|---|---|---|---|
| 3,730,179 | A | 5/1973 | Williams |
| 3,802,431 | A | 4/1974 | Farr |
| 3,841,319 | A | 10/1974 | Michael et al. |
| 3,905,361 | A | 9/1975 | Hewson et al. |
| 4,248,218 | A | 2/1981 | Fischer |
| 4,351,330 | A | 9/1982 | Scarberry |
| 4,421,296 | A | 12/1983 | Stephens |
| 4,506,665 | A | 3/1985 | Andrews et al. |
| 4,535,765 | A | 8/1985 | Paoluccio et al. |
| 4,579,114 | A | 4/1986 | Gray et al. |
| 4,951,661 | A | 8/1990 | Sladek |
| 4,960,128 | A | 10/1990 | Gordon et al. |
| 4,964,408 | A | 10/1990 | Hink et al. |
| 5,033,480 | A | 7/1991 | Wiley et al. |
| 5,038,766 | A | 8/1991 | Parker |
| 5,046,491 | A | 9/1991 | Derrick |
| 5,123,410 | A | 6/1992 | Greene et al. |
| 5,174,284 | A | 12/1992 | Jackson |
| 5,215,538 | A | 6/1993 | Larkin |
| 5,269,771 | A | 12/1993 | Thomas et al. |
| 5,273,032 | A | 12/1993 | Borody |
| 5,319,355 | A | 6/1994 | Russek |
| 5,337,744 | A | 8/1994 | Branigan |
| 5,341,805 | A | 8/1994 | Stavridi et al. |
| 5,353,837 | A | 10/1994 | Faust |
| D353,195 | S | 12/1994 | Savage et al. |
| D353,196 | S | 12/1994 | Savage et al. |
| 5,377,676 | A | 1/1995 | Vari et al. |
| 5,413,095 | A | 5/1995 | Weaver |
| D359,546 | S | 6/1995 | Savage et al. |
| 5,431,158 | A | 7/1995 | Tirotta |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,494,043 | A | 2/1996 | O'Sullivan et al. |
| 5,513,634 | A | 5/1996 | Jackson |
| 5,533,511 | A | 7/1996 | Kaspari et al. |
| 5,533,523 | A | 7/1996 | Bass, Jr. et al. |
| 5,561,275 | A | 10/1996 | Savage et al. |
| 5,590,649 | A | 1/1997 | Caro et al. |
| 5,602,924 | A | 2/1997 | Durand et al. |
| 5,620,408 | A | 4/1997 | Vennes et al. |
| 5,638,816 | A | 6/1997 | Kiani-Azarbayjany et al. |
| 5,638,818 | A | 6/1997 | Diab et al. |
| 5,645,046 | A | 7/1997 | Kay |
| 5,645,440 | A | 7/1997 | Tobler et al. |
| 5,671,914 | A | 9/1997 | Kalkhoran et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,752,510 | A | 5/1998 | Goldstein |
| 5,758,644 | A | 6/1998 | Diab et al. |
| 5,760,910 | A | 6/1998 | Lepper, Jr. et al. |
| 5,846,182 | A | 12/1998 | Wolcott |
| 5,884,625 | A | 3/1999 | Hart |
| 5,888,195 | A | 3/1999 | Schneider |
| 5,890,929 | A | 4/1999 | Mills et al. |
| 5,919,134 | A | 7/1999 | Diab |
| 5,950,624 | A | 9/1999 | Hart |
| 5,976,072 | A | 11/1999 | Greenberg |
| 5,987,343 | A | 11/1999 | Kinast |
| 5,997,343 | A | 12/1999 | Mills et al. |
| 6,002,952 | A | 12/1999 | Diab et al. |
| 6,010,937 | A | 1/2000 | Karam et al. |
| 6,012,455 | A | 1/2000 | Goldstein |
| 6,014,972 | A | 1/2000 | Sladek |
| 6,027,452 | A | 2/2000 | Flaherty et al. |
| 6,040,578 | A | 3/2000 | Malin et al. |
| 6,063,062 | A | 5/2000 | Paradis |
| 6,066,204 | A | 5/2000 | Haven |
| 6,089,541 | A | 7/2000 | Weinheimer et al. |
| 6,098,617 | A | 8/2000 | Connell |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,152,754 | A | 11/2000 | Gerhardt et al. |
| 6,184,521 | B1 | 2/2001 | Coffin, IV et al. |
| 6,206,003 | B1 | 3/2001 | Burch |
| 6,232,609 | B1 | 5/2001 | Snyder et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,257,238 | B1 | 7/2001 | Meah |
| 6,280,381 | B1 | 8/2001 | Malin et al. |
| 6,285,896 | B1 | 9/2001 | Tobler et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,334,065 | B1 | 12/2001 | Al-Ali et al. |
| 6,360,114 | B1 | 3/2002 | Diab et al. |
| 6,368,283 | B1 | 4/2002 | Xu et al. |
| 6,379,312 | B2 | 4/2002 | O'Toole |
| 6,411,373 | B1 | 6/2002 | Garside et al. |
| 6,415,167 | B1 | 7/2002 | Blank et al. |
| 6,422,240 | B1 | 7/2002 | Levitsky et al. |
| 6,430,437 | B1 | 8/2002 | Marro |
| 6,430,525 | B1 | 8/2002 | Weber et al. |
| 6,437,316 | B1 | 8/2002 | Colman et al. |
| RE37,861 | E | 9/2002 | Schneider |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,505,059 | B1 | 1/2003 | Kollias et al. |
| 6,517,549 | B1 | 2/2003 | Dennis |
| 6,525,386 | B1 | 2/2003 | Mills et al. |
| 6,526,300 | B1 | 2/2003 | Kiani et al. |
| 6,533,761 | B2 | 3/2003 | Bertoch et al. |
| 6,534,012 | B1 | 3/2003 | Hazen et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,606,511 | B1 | 8/2003 | Ali et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,656,127 | B1 | 12/2003 | Ben-Oren et al. |
| 6,658,276 | B2 | 12/2003 | Kiani et al. |
| 6,661,161 | B1 | 12/2003 | Lanzo et al. |
| 6,679,265 | B2 | 1/2004 | Strickland et al. |
| 6,697,656 | B1 | 2/2004 | Al-Ali |
| 6,697,658 | B2 | 2/2004 | Al-Ali |
| RE38,476 | E | 3/2004 | Diab et al. |
| RE38,492 | E | 4/2004 | Diab et al. |
| 6,738,652 | B2 | 5/2004 | Mattu et al. |
| 6,758,212 | B2 | 7/2004 | Swann |
| 6,760,607 | B2 | 7/2004 | Al-Ali |
| 6,766,800 | B2 | 7/2004 | Chu et al. |
| 6,788,965 | B2 | 9/2004 | Ruchti et al. |
| 6,816,241 | B2 | 11/2004 | Grubisic |
| 6,822,564 | B2 | 11/2004 | Al-Ali |
| 6,850,787 | B2 | 2/2005 | Weber et al. |
| 6,850,788 | B2 | 2/2005 | Al-Ali |
| 6,876,931 | B2 | 4/2005 | Lorenz et al. |
| 6,920,345 | B2 | 7/2005 | Al-Ali et al. |
| 6,934,570 | B2 | 8/2005 | Kiani et al. |
| 6,943,348 | B1 | 9/2005 | Coffin, IV |
| 6,956,649 | B2 | 10/2005 | Acosta et al. |
| 6,961,598 | B2 | 11/2005 | Diab |
| 6,969,357 | B1 | 11/2005 | Colman et al. |
| 6,970,792 | B1 | 11/2005 | Diab |

(56) References Cited

U.S. PATENT DOCUMENTS 6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D523,994 S 6/2006 Manzo
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
D536,441 S 2/2007 Garren et al.
D538,926 S 3/2007 Jeong et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,383,839 B2 6/2008 Porat et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
7,488,229 B2 2/2009 Ben-Oren et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,530,984 B2 5/2009 Sonnenschein et al.
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D605,285 S 12/2009 Garren et al.
D606,659 S 12/2009 Kiani et al.
7,624,736 B2 12/2009 Borody
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,727,194 B2 6/2010 Nalagatla et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,766,008 B2 8/2010 Manishen
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,934,505 B2 5/2011 Garren et al.
7,937,128 B2 5/2011 Al-Ali
7,937,129 B2 5/2011 Mason et al.
7,941,199 B2 5/2011 Kiani
7,946,288 B2 5/2011 Flynn et al.
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,028,704 B2 10/2011 Reynolds et al.
8,048,040 B2 11/2011 Kiani
8,050,728 B2 11/2011 Al-Ali et al.
8,083,672 B2 12/2011 Minson
RE43,169 E 2/2012 Parker
D654,173 S 2/2012 Farrell
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,240,187 B2 8/2012 Colman et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,297,275 B2 10/2012 Ogilvie et al.
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,095 B2 4/2013 Inoue et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,460,248 B2 6/2013 Ryan et al.
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
8,534,278 B2 9/2013 Colman et al.
D692,145 S 10/2013 Al-Ali et al.
8,555,886 B2 10/2013 Colman et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,684,919 B2 4/2014 Anca et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.

(56) References Cited

U.S. PATENT DOCUMENTS

| | | | |
|---|---|---|---|
| 8,755,535 | B2 | 6/2014 | Telfort et al. |
| 8,755,872 | B1 | 6/2014 | Marinow |
| 8,764,671 | B2 | 7/2014 | Kiani |
| 8,768,423 | B2 | 7/2014 | Shakespeare et al. |
| 8,770,189 | B2 | 7/2014 | Colman et al. |
| 8,771,204 | B2 | 7/2014 | Telfort et al. |
| 8,781,544 | B2 | 7/2014 | Al-Ali et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,840,549 | B2 | 9/2014 | Al-Ali et al. |
| 8,852,094 | B2 | 10/2014 | Al-Ali et al. |
| 8,852,994 | B2 | 10/2014 | Wojtczuk et al. |
| 8,897,847 | B2 | 11/2014 | Al-Ali |
| 8,911,377 | B2 | 12/2014 | Al-Ali |
| 8,973,573 | B2 | 3/2015 | Filipi |
| 8,989,831 | B2 | 3/2015 | Al-Ali et al. |
| 8,998,809 | B2 | 4/2015 | Kiani |
| 9,044,565 | B2 | 6/2015 | Colman et al. |
| 9,060,680 | B2 | 6/2015 | Colman et al. |
| 9,066,666 | B2 | 6/2015 | Kiani |
| 9,066,680 | B1 | 6/2015 | Al-Ali et al. |
| 9,084,861 | B2 | 7/2015 | Tseng et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,131,881 | B2 | 9/2015 | Diab et al. |
| 9,132,254 | B2 | 9/2015 | Anca et al. |
| 9,138,180 | B1 | 9/2015 | Coverston et al. |
| 9,153,112 | B1 | 10/2015 | Kiani et al. |
| 9,186,473 | B2 | 11/2015 | Colman et al. |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,095 | B1 | 12/2015 | Al-Ali |
| 9,218,454 | B2 | 12/2015 | Kiani et al. |
| 9,245,668 | B1 | 1/2016 | Vo et al. |
| 9,267,572 | B2 | 2/2016 | Barker et al. |
| 9,277,880 | B2 | 3/2016 | Poeze et al. |
| 9,302,089 | B2 | 4/2016 | Besko |
| 9,307,891 | B2 | 4/2016 | Carter et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,345,435 | B1 | 5/2016 | DelAguila |
| 9,392,945 | B2 | 7/2016 | Al-Ali et al. |
| 9,399,106 | B2 | 7/2016 | Borody |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,498,150 | B2 | 11/2016 | Colman et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,669,174 | B2 | 6/2017 | Isenberg et al. |
| 9,669,175 | B2 | 6/2017 | Olympio |
| 9,687,623 | B2 | 6/2017 | Colman et al. |
| 9,697,928 | B2 | 7/2017 | Al-Ali et al. |
| 9,706,965 | B2 | 7/2017 | Colman et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,749,232 | B2 | 8/2017 | Sampath et al. |
| 9,750,442 | B2 | 9/2017 | Olsen |
| 9,750,461 | B1 | 9/2017 | Telfort |
| 9,757,052 | B2 | 9/2017 | Levitsky et al. |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,849,259 | B2 | 12/2017 | Colman et al. |
| D807,583 | S | 1/2018 | Evans |
| 9,861,298 | B2 | 1/2018 | Eckerbom et al. |
| 9,861,305 | B1 | 1/2018 | Weber et al. |
| 9,867,957 | B2 | 1/2018 | Colman et al. |
| 9,877,650 | B2 | 1/2018 | Muhsin et al. |
| 9,891,079 | B2 | 2/2018 | Dalvi |
| 9,924,897 | B1 | 3/2018 | Abdul-Hafiz |
| 9,936,917 | B2 | 4/2018 | Poeze et al. |
| 9,955,937 | B2 | 5/2018 | Telfort |
| 9,965,946 | B2 | 5/2018 | Al-Ali et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,070,826 | B2 | 9/2018 | Colman et al. |
| D829,916 | S | 10/2018 | Eaton |
| 10,086,138 | B1 | 10/2018 | Novak, Jr. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,219,686 | B2 | 3/2019 | Lin et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,252,018 | B2 | 4/2019 | Chaudhry |
| D849,956 | S | 5/2019 | Demarest et al. |
| 10,279,247 | B2 | 5/2019 | Kiani |
| 10,285,571 | B2 | 5/2019 | Rozenfeld et al. |
| 10,292,664 | B2 | 5/2019 | Al-Ali |
| 10,299,720 | B2 | 5/2019 | Brown et al. |
| 10,300,234 | B2 | 5/2019 | Colman et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| 10,390,734 | B2 | 8/2019 | Johnson et al. |
| 10,413,689 | B2 | 9/2019 | Eaton et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| D869,774 | S | 12/2019 | Turkbas |
| 10,505,311 | B2 | 12/2019 | Al-Ali et al. |
| D873,410 | S | 1/2020 | Scampoli et al. |
| 10,524,738 | B2 | 1/2020 | Olsen |
| 10,532,174 | B2 | 1/2020 | Al-Ali |
| 10,537,285 | B2 | 1/2020 | Shreim et al. |

(56) References Cited

U.S. PATENT DOCUMENTS

| | | | |
|---|---|---|---|
| 10,542,903 | B2 | 1/2020 | Al-Ali et al. |
| D876,728 | S | 2/2020 | Evans et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,709,858 | B2 | 7/2020 | McDonald et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,780,240 | B2 | 9/2020 | Isenberg et al. |
| 10,806,327 | B2 | 10/2020 | Brain |
| 10,820,834 | B2 | 11/2020 | Levitsky et al. |
| 10,827,910 | B2 | 11/2020 | Svärd |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf |
| D906,970 | S | 1/2021 | Forrest et al. |
| D908,213 | S | 1/2021 | Abdul-Hafiz et al. |
| D909,586 | S | 2/2021 | Farrell |
| 10,912,622 | B2 | 2/2021 | Meah |
| 10,918,281 | B2 | 2/2021 | Al-Ali et al. |
| 10,925,988 | B2 | 2/2021 | Kertser et al. |
| 10,932,692 | B2 | 3/2021 | Kertser |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,987,476 | B2 | 4/2021 | Chaudhry |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |

(56) References Cited

U.S. PATENT DOCUMENTS 12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin et al.
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
12,538,084 B1 1/2026 Telfort et al.
12,539,046 B2 2/2026 Kiani
D1,119,639 S 3/2026 Al-Ali et al.
12,575,797 B2 3/2026 Olsen et al.
D1,124,008 S 4/2026 Indorf et al.
D1,124,017 S 4/2026 Indorf et al.
D1,124,917 S 5/2026 Al-Ali et al.
12,616,623 B1 5/2026 Al-Ali et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0121520 A1 7/2003 Parker et al.
2003/0144582 A1 7/2003 Cohen et al.
2003/0154987 A1* 8/2003 Palmer ............. A61M 16/0672 128/207.14
2003/0156288 A1 8/2003 Barnum et al.
2003/0208103 A1 11/2003 Sonnenschein
2003/0212312 A1 11/2003 Coffin, IV et al.
2004/0106163 A1 6/2004 Workman, Jr. et al.
2004/0129272 A1 7/2004 Ganesh et al.
2004/0129273 A1 7/2004 Hickle
2004/0249367 A1 12/2004 Saadat et al.
2005/0028811 A1 2/2005 Nelson et al.
2005/0055276 A1 3/2005 Kiani et al.
2005/0087715 A1 4/2005 Doyle
2005/0165304 A1 7/2005 Albertelli
2005/0234317 A1 10/2005 Kiani
2006/0042637 A1 3/2006 Martin et al.
2006/0073719 A1 4/2006 Kiani
2006/0189871 A1 8/2006 Al-Ali et al.
2006/0207597 A1 9/2006 Wright
2006/0231091 A1 10/2006 Camarillo
2007/0006878 A1 1/2007 Mackey et al.
2007/0073116 A1 3/2007 Kiani et al.
2007/0113844 A1 5/2007 Garren et al.
2007/0135770 A1 6/2007 Hunt et al.
2007/0180140 A1 8/2007 Welch et al.
2007/0244377 A1 10/2007 Cozad et al.
2007/0272247 A1 11/2007 Porat
2008/0053434 A1 3/2008 Wightman et al.
2008/0064965 A1 3/2008 Jay et al.
2008/0094228 A1 4/2008 Welch et al.
2008/0103375 A1 5/2008 Kiani
2008/0110456 A1 5/2008 Flynn et al.
2008/0221418 A1 9/2008 Al-Ali et al.
2008/0230054 A1 9/2008 Prineas
2008/0275357 A1 11/2008 Porat et al.
2009/0036759 A1 2/2009 Ault et al.
2009/0064998 A1 3/2009 Bassili
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0130821 A1 5/2010 Rosemurgy et al.
2010/0132700 A1 6/2010 Filipi et al.
2010/0198096 A1 8/2010 Colman et al.
2010/0234718 A1 9/2010 Sampath et al.
2010/0262033 A1* 10/2010 Colman ............. A61B 1/00154 600/532
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283513 A1* 11/2012 Leeflang ............. A61M 16/208 600/114
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0131446 A1 5/2013 Dryden, Jr. et al.
2013/0296672 A1 11/2013 O'Neil et al.
2013/0345921 A1 12/2013 Al-Ali et al.
2014/0081084 A1 3/2014 Domenico et al.
2014/0166076 A1 6/2014 Kiani et al.
2014/0180160 A1 6/2014 Brown et al.
2014/0187973 A1 7/2014 Brown et al.
2014/0196726 A1 7/2014 Mallek
2014/0246030 A1 9/2014 Puri et al.
2014/0275784 A1 9/2014 Joyce
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0068538 A1 3/2015 Wesolowski et al.
2015/0073241 A1 3/2015 Lamego
2015/0080754 A1 3/2015 Purdon et al.
2015/0099950 A1 4/2015 Al-Ali et al.
2015/0107600 A1 4/2015 Jackson et al.
2015/0119742 A1 4/2015 Tse et al.
2015/0190599 A1 7/2015 Colman et al.

(56) References Cited

U.S. PATENT DOCUMENTS

2015/0208952 A1 7/2015 Addison
2015/0265792 A1 9/2015 Goudra et al.
2016/0022129 A1 1/2016 Colman et al.
2016/0082211 A1 3/2016 Chedid et al.
2016/0196388 A1 7/2016 Lamego
2016/0228035 A1 8/2016 Poormand et al.
2016/0243329 A1 8/2016 Chen
2016/0256652 A1* 9/2016 Wiesman ............... A61B 5/082
2016/0296719 A1* 10/2016 Geraghty .......... A61M 16/0486
2016/0367173 A1 12/2016 Dalvi et al.
2017/0000586 A1 1/2017 Lesser
2017/0024748 A1 1/2017 Haider
2017/0173632 A1 6/2017 Al-Ali
2017/0197052 A1 7/2017 Tylka et al.
2017/0251974 A1 9/2017 Shreim et al.
2018/0242926 A1 8/2018 Muhsin et al.
2018/0247712 A1 8/2018 Muhsin et al.
2019/0105452 A1 4/2019 Takatori et al.
2019/0117922 A1 4/2019 Poulsen et al.
2019/0125213 A1 5/2019 Rockwell et al.
2019/0232003 A1 8/2019 Chaudhry
2019/0239787 A1 8/2019 Pauley et al.
2019/0298956 A1 10/2019 Takatori et al.
2019/0320906 A1 10/2019 Olsen
2019/0320938 A1 10/2019 Narkiss
2019/0374713 A1 12/2019 Kiani et al.
2020/0060869 A1 2/2020 Telfort et al.
2020/0111552 A1 4/2020 Ahmed
2020/0113435 A1 4/2020 Muhsin
2020/0113496 A1 4/2020 Scruggs et al.
2020/0113520 A1 4/2020 Abdul-Hafiz et al.
2020/0138368 A1 5/2020 Kiani et al.
2020/0163597 A1 5/2020 Dalvi et al.
2020/0178767 A1 6/2020 Miller
2020/0178773 A1 6/2020 Miller
2020/0179632 A1 6/2020 Worley
2020/0196877 A1 6/2020 Vo et al.
2020/0253474 A1 8/2020 Muhsin et al.
2020/0253544 A1 8/2020 Belur Nagaraj et al.
2020/0261677 A1 8/2020 Bezerra
2020/0275841 A1 9/2020 Telfort et al.
2020/0282164 A1* 9/2020 Thomas ............ A61M 16/0431
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2020/0384228 A1 12/2020 Garbagnati
2021/0022628 A1 1/2021 Telfort et al.
2021/0023319 A1 1/2021 Brar
2021/0023321 A1 1/2021 Brar
2021/0077293 A1 3/2021 Ogle et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0121653 A1 4/2021 Mckay
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0066246 A1* 2/2024 Slaughter ............ A61M 16/085
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.
2025/0318761 A1 10/2025 Al-Ali et al.
2025/0322950 A1 10/2025 Al-Ali et al.
2025/0323417 A1 10/2025 Rey
2025/0329240 A1 10/2025 Kiani
2025/0344010 A1 11/2025 Al-Ali et al.
2026/0014333 A1 1/2026 Fernkvist et al.

(56) References Cited

U.S. PATENT DOCUMENTS

| | | | |
|---|---|---|---|
| 2026/0014334 A1 | 1/2026 | Danwihl | |
| 2026/0048198 A1 | 2/2026 | Vo et al. | |

FOREIGN PATENT DOCUMENTS

| | | |
|---|---|---|
| DE | 37 19 009 | 12/1988 |
| DE | 199 44 242 | 3/2001 |
| DE | 101 40 291 | 8/2002 |
| EP | 0 856 327 | 8/1998 |
| EP | 3 106 078 | 5/2019 |
| EP | 3 679 973 | 7/2020 |
| JP | 2000-060981 | 2/2000 |
| WO | WO 91/014469 | 10/1991 |
| WO | WO 92/011053 | 7/1992 |
| WO | WO 99/038432 | 8/1999 |
| WO | WO 02/096342 | 12/2002 |
| WO | WO 2004/030723 | 4/2004 |
| WO | WO 2004/052438 | 6/2004 |
| WO | WO 2005/016142 | 2/2005 |

OTHER PUBLICATIONS

US 2024/0016391 A1, 01/2024, Lapotko et al. (withdrawn)

Amazon, "2PCS Silicone Teeth Mouth Opener", first available Jun. 24, 2022, https://www.amazon.com/dp/BOB51 M6N5B/.

Amazon, "Endure Disposable Medical Bite Block", first available Jul. 18, 2022, https://www.amazon.com/Endure-Disposable-Protector-Management-Endoscopy/dp/BOB6WQG1QW.

Amazon, "Mouth Opener", first available Jan. 16, 2022, https://www.amazon.com/dp/B09QK468H3/.

Youtube, "Carbo Track with Bite Block", first available Nov. 27, 2017, https://www.youtube.com/watch?v=aFJeHxFnKik.

* cited by examiner

BITE BLOCK AND ASSEMBLIES INCLUDING SAME

INCORPORATION BY REFERENCE TO ANY PRIORITY APPLICATIONS

This application claims priority to U.S. Provisional Application No. 63/262,235, filed Oct. 7, 2021, entitled "Bite Block and Assemblies Including Same," which is incorporated by reference herein in its entirety.

TECHNICAL FIELD

The present disclosure relates to the field of bite blocks and bite block assemblies for use during endoscopic procedures.

BACKGROUND

Upper endoscopy procedures are utilized to investigate, diagnose, and/or treat medical conditions relating to the upper digestive system. Such procedures typically require a flexible endoscopic tube to be inserted through the mouth, esophagus, stomach, and duodenum. Patients are often positioned on one of their sides and sedated for a period of time depending on the type of procedure. Bite blocks are often employed to prevent sedated patients from biting and damaging the endoscopic tube during the procedure.

SUMMARY

Disclosed herein is a bite block assembly for providing gases to a subject and sampling exhaled gases from the subject during an endoscopic procedure. In some implementations, the bite block assembly comprises a bite block and a nasal cannula assembly. In some implementations, the bite block comprises a main body and a mouthpiece extending outward from the main body and configured to be positioned in a mouth of the subject when the bite block is in use. In some implementations, the mouthpiece comprises a main channel configured to receive an endoscopic tube and a sampling channel configured to receive orally exhaled gases from the subject. In some implementations, the nasal cannula assembly comprises: a nasal cannula manifold comprising a first end, a second end opposite the first end, a first interior portion, a second interior portion, a wall separating the first and second interior portions, and an opening in fluid communication with the second interior portion; a first gas delivery tube connected to the first end of the nasal cannula manifold and in fluid communication with the first interior portion of the nasal cannula manifold; a first nasal prong in fluid communication with the first interior portion of the nasal cannula manifold and configured to direct gases from the first gas delivery tube into a first nostril of the subject; a second nasal prong in fluid communication with the second interior portion of the nasal cannula manifold and configured to receive gases exhaled from a second nostril of the subject; a scoop configured to be connected to the nasal cannula manifold and direct said orally exhaled gases from the sampling channel of the bite block to the opening of the nasal cannula manifold; and a gas sampling tube. In some implementations, the scoop comprises: a body comprising a first surface and a second surface opposite the first surface, the first surface configured to face at least partially toward the sampling channel of the bite block when the bite block assembly is in use; and a rib extending outward from and along a portion of the first surface of the body, the rib defining a fluid passage configured to receive and direct said orally exhaled gases towards the opening of the nasal cannula manifold. The gas sampling tube can be connected to the second end of the nasal cannula manifold and in fluid communication with the second interior portion of the nasal cannula manifold. The gas sampling tube can be configured to direct said gases exhaled from the second nostril and said orally exhaled gases to a gas monitoring device.

In some implementations: the body of the scoop comprises a basin shape; the first surface comprises an interior surface of the basin shaped body and the second surface comprises an exterior surface of the basin shaped body; the basin shaped body further comprises an edge surface between the interior and exterior surfaces and extending along a plane; and the rib is spaced inward from said plane. In some implementations, the rib comprises an opening into the fluid passage of the rib, and wherein said opening of the rib faces away from the interior surface of the basin shaped body. In some implementations, an axis extending through a center of the opening of the rib is substantially perpendicular relative to a portion of the interior surface of the basin shaped body. In some implementations: the rib comprises a first end, a second end, and a length extending between the first and second ends; the first end of the rib terminates at a portion of the interior surface that is spaced inward from the edge surface of the basin shaped body; and an axis extending through a center of the opening of the rib is substantially perpendicular relative to the portion of the interior surface. In some implementations: the fluid passage of the rib comprises a first portion and a second portion, the first portion comprising said opening of the rib; and the first and second portions of the fluid passage of the rib are oriented transverse relative to one another. In some implementations, the first and second portions of the fluid passage of the rib are oriented substantially perpendicular relative to one another.

In some implementations, the scoop further comprises a connector extending outward from the body of the scoop and configured to connect to a portion of the nasal cannula manifold. In some implementations, said connector of the scoop is configured to secure within the opening of the nasal cannula manifold, and wherein said connector comprises a fluid passage in fluid communication with the fluid passage of the rib of the scoop. In some implementations, the rib comprises an opening into the fluid passage of the rib, and wherein the fluid passage of said connector is oriented transverse relative to the opening of the rib.

In some implementations, the bite block assembly further comprises: a second gas delivery tube configured to receive gases from a gas source; a branched connector comprising a first branch configured to be connected to the second gas delivery tube, a second branch configured to be connected to said first gas delivery tube, and a third branch configured to be connected to a third gas delivery tube; said third gas delivery tube; and a gas delivery channel in a portion of the bite block and configured to receive a portion of said third gas delivery tube; wherein the branched connector is configured to direct gases from said second gas delivery tube to the first and third gas delivery tubes when connected therewith. In some implementations, said first branch is permanently secured to said second gas delivery tube. In some implementations, said second branch is permanently secured to said first gas delivery tube. In some implementations, said third branch is configured to be removably connected to said third gas delivery tube.

In some implementations, said third gas delivery tube comprises a first end and a second end, said first end permanently secured within said gas delivery channel in the portion of the bite block. In some implementations, said second end of said third gas delivery tube is configured to be removably connected to said third branch. In some implementations, the bite block assembly further comprises a connector secured to the second end of said third gas delivery tube and having a tapered end configured to secure within the third branch. In some implementations, the bite block assembly further comprises a cap secured to the third branch, wherein the cap is configured to be transitioned from a first configuration in which the cap prevents gases from flowing out of the third branch to a second configuration in which the cap allows gases to flow out of the third branch. In some implementations, the cap comprises a base secured to the third branch, a lid, and a hinge between the base and lid and configured to allow the lid to move between an open position and a closed position. In some implementations, the cap further comprises a plug extending outward from the lid and configured to secure within an opening in the third branch when the lid in in the closed position.

In some implementations, said gas delivery channel is in fluid communication with the main channel of the bite block. In some implementations, an axis extending through a center of said gas delivery channel is oriented transverse relative to an axis extending through a center of said main channel. In some implementations, said gas delivery channel opens into the main channel. In some implementations, said gas delivery channel is formed from a recess on a portion of a surface of the main body and a hole extending through the main body and through a portion of the mouthpiece.

In some implementations: said main body of said bite block comprises an opening in fluid communication with the sampling channel of the mouthpiece; said bite block further comprises a pocket wall extending outward from the main body and around said opening in the main body; and said scoop is configured to fit at least partially within an interior space defined by said pocket wall and direct said orally exhaled gases from the sampling channel to the opening of the nasal cannula manifold.

In some implementations, the nasal cannula manifold comprises a first arm, a second arm, and a body positioned between the first and second arms, and wherein the first and second nasal prongs extend from the body. In some implementations, each of the first and second arms comprises a bent portion. In some implementations, the first and second arms are removably connectable to the body. In some implementations, the first gas delivery tube is connected to the first arm and wherein the gas sampling tube is connected to the second arm.

In some implementations, the opening of the nasal cannula manifold is in said body. In some implementations, the nasal cannula manifold further comprises a connector extending outward from the body and configured to receive and secure a connector of the scoop. In some implementations, the connector of the nasal cannula manifold and the connector of the scoop connect in a friction fit arrangement. In some implementations, an interior of the connector of the nasal cannula manifold is in fluid communication with the opening of the nasal cannula manifold.

In some implementations, the nasal cannula manifold further comprises a connector configured to receive and secure a connector of the scoop. In some implementations, the connector of the nasal cannula manifold and the connector of the scoop connect in a friction fit arrangement. In some implementations, an interior of the connector of the nasal cannula manifold is in fluid communication with the opening of the nasal cannula manifold. In some implementations, the bite block assembly further comprises a flange extending outward from a portion of the nasal cannula manifold and configured to assist in positioning the scoop relative to the nasal cannula manifold when the scoop is connected to the nasal cannula manifold. In some implementations, the bite block assembly further comprises a wall extending through a portion of the mouthpiece and configured to divide the main channel from the sampling channel. In some implementations, the mouthpiece comprises a first end connected to the main body, a second end opposite the first end, and a length extending between the first and second ends, wherein a length of the sampling channel is less than the length of the mouthpiece.

In some implementations, the main body of the bite block comprises a first wing, a second wing, and an intermediate portion between the first and second wings, and wherein the first and second wings are configured to extend laterally away from the subject's mouth and contact the subject's face when the mouthpiece is positioned in the subject's mouth. In some implementations, the bite block assembly further comprises a strap configured to secure the bite block to the subject's head, wherein each of the first and second wings comprises a hook configured to attach to a portion of the strap.

Disclosed herein is a bite block assembly for providing gases to a subject and sampling exhaled gases from the subject during an endoscopic procedure. In some implementations, the bite block assembly comprises a bite block and a nasal cannula assembly. In some implementations, the bite block comprises a main body and a mouthpiece extending outward from the main body and configured to be positioned in a mouth of the subject when the bite block is in use. In some implementations, the mouthpiece comprises: a main channel configured to receive an endoscopic tube; and a sampling channel configured to receive orally exhaled gases from the subject. In some implementations, the nasal cannula assembly comprises: a nasal cannula manifold comprising a manifold body, a first nasal prong extending outward from the manifold body, and a second nasal prong extending outward from the manifold body and spaced from the first nasal prong, wherein a first portion of the manifold body is configured to direct gases received from a gas delivery tube to the first nasal prong, and wherein a second portion of the manifold body is configured to direct exhaled gases received by the second nasal prong to a gas sampling tube; and a scoop configured to be connected to the nasal cannula manifold and direct said orally exhaled gases from the sampling channel of the bite block to the second portion of the manifold body. In some implementations, the scoop comprises: a body comprising a first surface and a second surface opposite the first surface, the first surface configured to face at least partially toward the sampling channel of the bite block when the bite block assembly is in use; and a rib extending outward from and along a portion of the first surface of the body, the rib defining a fluid passage configured to receive and direct said orally exhaled gases towards the second portion of the manifold body.

In some implementations, the first portion of the manifold body is not in fluid communication with the second portion of the manifold body. In some implementations, the manifold body further comprises an inner wall that partitions an interior of the manifold body into the first and second portions. In some implementations, the nasal cannula assembly further comprises said gas delivery tube, and wherein said gas delivery tube is connected to a first end of the manifold body and is configured to receive gases from a gas source. In some implementations, the nasal cannula assembly further comprises said gas sampling tube, and wherein said gas sampling tube is connected to a second end of the manifold body and is configured to direct said gases exhaled from the subject to a gas monitoring device. In some implementations, the manifold body further comprises an opening in fluid communication with the second portion of the manifold body, and wherein the fluid passage of the rib of the scoop is in fluid communication with the opening and second portion of the manifold body when the scoop is connected to the nasal cannula manifold.

Disclosed herein is a bite block comprising: a main body comprising a first surface and a second surface opposite the first surface; and a mouthpiece extending outward from the second surface of the main body and configured to be positioned in a mouth of the subject when the bite block is in use. In some implementations, the mouthpiece comprises: a main channel configured to receive an endoscopic tube; and a sampling channel configured to receive orally exhaled gases from the subject. In some implementations, the bite block further comprises a gas delivery channel configured to direct gases into the subject's mouth when the bite block is in use, the gas delivery channel extending through a portion of the main body and through a portion of the main channel such that the gas delivery channel is in fluid communication with the main channel. In some implementations, the bite block further comprises a recess extending along a portion of the first surface of the main body proximate the gas delivery channel, wherein the recess is configured to receive a portion of a gas delivery tube.

In some implementations, an axis extending through a center of the gas delivery channel is transverse relative to an axis extending through a center of the main channel. In some implementations, the bite block further comprises a tube clip extending outward from a portion of the main body, the tube clip configured to secure a portion of the gas delivery tube. In some implementations: the main body further comprises a first wing, a second wing, and an intermediate portion between the first and second wings; the first and second wings are configured to extend laterally away from the subject's mouth and contact the subject's face when the mouthpiece is positioned in the subject's mouth; the tube clip extending outward from the first surface and the first wing of the main body. In some implementations, the tube clip comprises a first arm and a second arm spaced from the first arm, and wherein free ends of the first and second arms are spaced away from one another by a gap, thereby allowing the first and second arms to be resiliently flexed to secure the portion of the gas delivery tube to the tube clip.

Disclosed herein is a bite block comprising a main body, a mouthpiece, and a gas delivery channel. The main body can comprise a first surface and a second surface opposite the first surface, a first wing, a second wing, and an intermediate portion between the first and second wings, the first and second wings extending laterally away from the intermediate portion. The mouthpiece can extend outward from the second surface of the main body and be positioned in a mouth of a subject when the bite block is in use. In some implementations, the first and second wings of the main body are configured to be positioned on opposite sides of the subject's mouth and adjacent the subject's face when the mouthpiece is positioned in the subject's mouth. In some implementations, the mouthpiece comprises: a main channel configured to receive an endoscopic tube; and a sampling channel configured to receive orally exhaled gases from the subject. The bite block can further comprise: a gas delivery channel configured to direct gases into the subject's mouth when the bite block is in use, the gas delivery channel extending through the intermediate portion of the main body and through a portion of the main channel of the mouthpiece such that the gas delivery channel is in fluid communication with the main channel. The bite block can further comprise: a gas delivery tube configured to deliver gases to the gas delivery channel, the gas delivery tube comprising a first end and a second end opposite the first end, wherein the second end is permanently secured within the gas delivery channel. The bite block can further comprise: a tube clip located on a portion of the first wing of the main body, the tube clip comprising a first arm and a second arm, each of the first and second arms extending outward from the first wing and having free ends that are separated from one another by a gap, wherein the first and second arms are configured to secure a first portion of the gas delivery tube. The bite block can further comprise: a recess extending along a portion of the first surface of the main body proximate the gas delivery channel, wherein the recess is configured to receive a second portion of the gas delivery tube when the first portion of the gas delivery tube is secured between the first and second arms of the tube clip.

In some implementations, an axis extending through a center of the gas delivery channel is transverse relative to an axis extending through a center of the main channel. In some implementations, a first end of the recess is located at the gas delivery channel and a second end of the recess is spaced away from the gas delivery channel. In some implementations, the recess extends from the first end to the second end, and wherein the second end of the recess is located at a junction where the first wing and the intermediate portion of the main body meet. In some implementations, the recess extends from the gas delivery channel along the intermediate portion and toward the first wing. In some implementations, the recess extends from the gas delivery channel along the intermediate portion and toward the tube clip. In some implementations, the recess comprises a substantially semi-circular cross-section. In some implementations, the recess is configured to surround less then an entire cross-section of the first portion of the gas delivery tube. In some implementations, the recess is configured to surround less then about ¾ of a cross-section of the first portion of the gas delivery tube. In some implementations, a first portion of the gas delivery channel comprises a first cross-section and a second portion of the gas delivery channel comprises a second cross-section that is different than the first cross-section. In some implementations, a ledge is defined at a juncture of the first and second cross-sections of the gas delivery channel, and wherein the second end of the gas delivery tube abuts the ledge.

Disclosed herein is a bite block comprising a main body and a mouthpiece. The main body can comprise a first surface and a second surface opposite the first surface. The mouthpiece can extend outward from the second surface of the main body and be configured to be positioned in a mouth of a subject when the bite block is in use. The mouthpiece can comprise: a main channel configured to receive an endoscopic tube; and a sampling channel configured to receive orally exhaled gases from the subject. The bite block can further comprise a gas delivery channel configured to direct gases into the subject's mouth when the bite block is in use, the gas delivery channel extending through a portion of the main channel of the mouthpiece such that the gas delivery channel is in fluid communication with the main channel. The bite block can further comprise a recess extending along a portion of the first surface of the main body proximate the gas delivery channel, wherein the recess is configured to receive a portion of a gas delivery tube.

In some implementations, an axis extending through a center of the gas delivery channel is transverse relative to an axis extending through a center of the main channel. In some implementations, a first end of the recess is located at the gas delivery channel and a second end of the recess is spaced away from the gas delivery channel. In some implementations, the main body comprises a first wing, a second wing, and an intermediate portion between the first and second wings, and wherein the second end of the recess is located at a junction where the first wing and the intermediate portion of the main body meet. In some implementations, the recess comprises a substantially semi-circular cross-section. In some implementations, the recess is configured to surround less then an entire cross-section of the portion of the gas delivery tube. In some implementations, the bite block further comprises a tube clip located on a portion of the main body, the tube clip comprising a first arm and a second arm, each of the first and second arms extending outward from the portion of the main body and having free ends that are separated from one another by a gap, wherein the first and second arms are configured to secure the gas delivery tube. In some implementations, a first portion of the gas delivery channel comprises a first cross-section and a second portion of the gas delivery channel comprises a second cross-section that is different than the first cross-section. In some implementations, the bite block further comprises said gas delivery tube, said gas delivery tube comprising a first end and a second end, wherein a ledge is defined at a juncture of the first and second cross-sections of the gas delivery channel, and wherein the second end of the gas delivery tube abuts the ledge.

For purposes of summarizing the disclosure, certain aspects, advantages and novel features of several devices, systems, and methods have been described herein. It is to be understood that not necessarily all examples of the present disclosure are disclosed herein. Thus, the devices, systems, and methods disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

DETAILED DESCRIPTION

Various embodiments will be described below in conjunction with the drawings for purposes of illustration. It should be appreciated that many other implementations of the disclosed concepts are possible, and various advantages can be achieved with the disclosed implementations.

Disclosed herein are bite block assemblies, bite blocks, nasal cannula assemblies, and components thereof which can be used during an endoscopic procedure to: deliver gases (for example, oxygen) to a subject's oral and/or nasal passages; and/or collect exhaled gases (which can include, for example, $CO_2$) from the subject's oral and/or nasal passages for analysis and/or monitoring, for example, for capnography and/or anesthetic gas measurements.

Figure 1A:
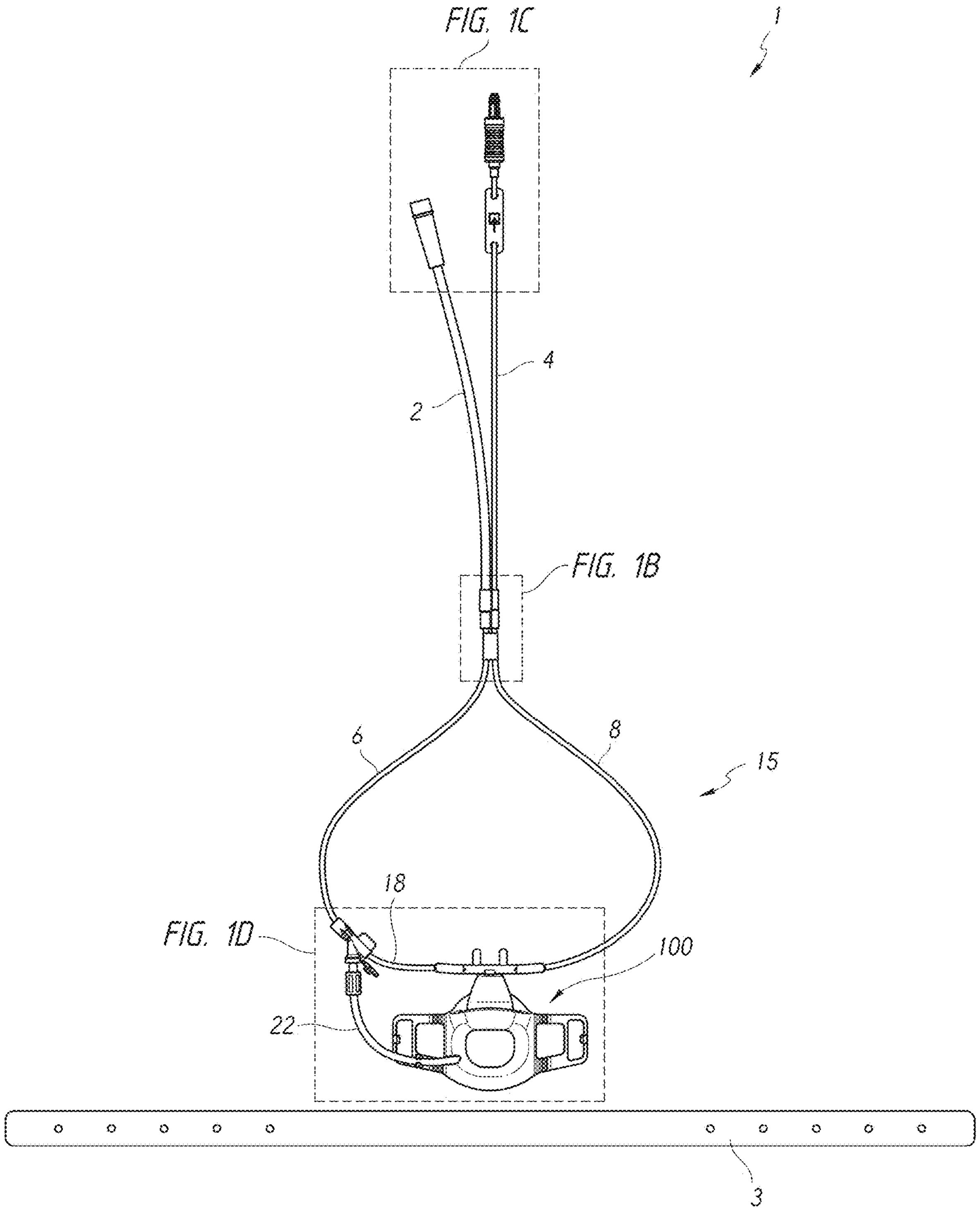
FIG. 1A illustrates a front view of a bite block assembly in accordance with aspects of this disclosure.
Figure 1B:
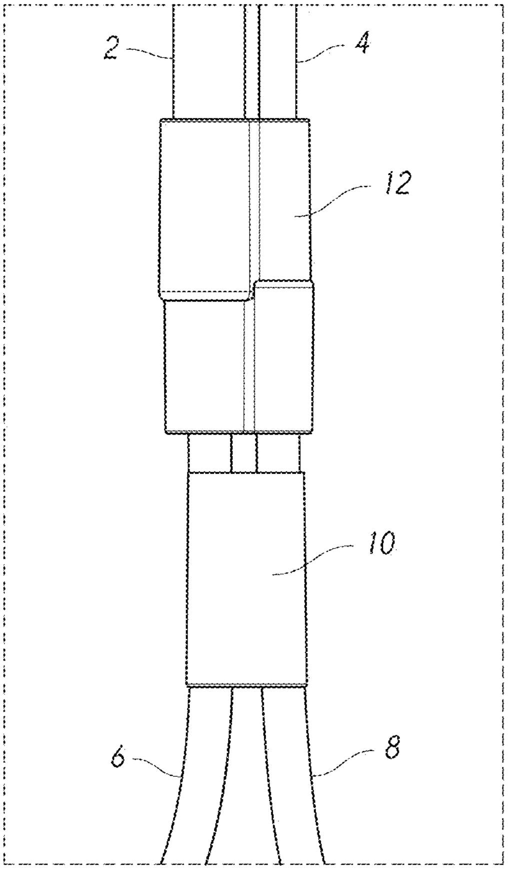
FIGS. 1B-1D illustrate enlarged views of portions of the bite block assembly of FIG. 1A in accordance with aspects of this disclosure.
Figure 1C:
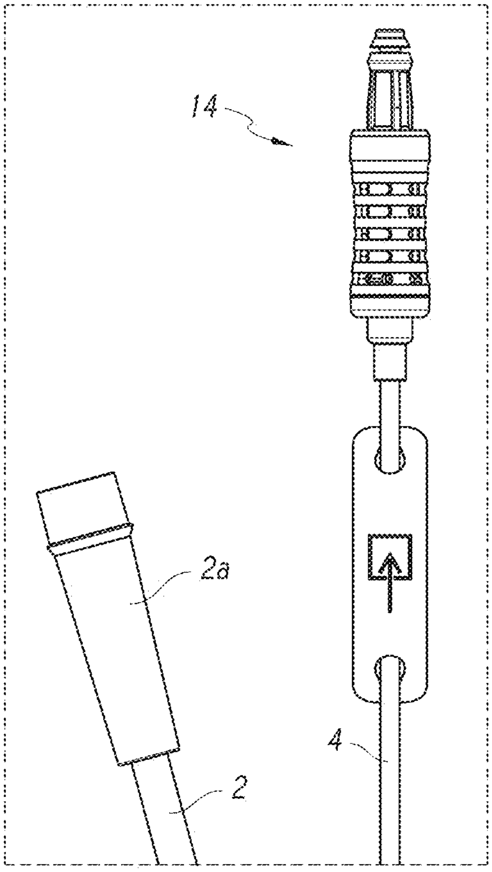
Figure 1D:
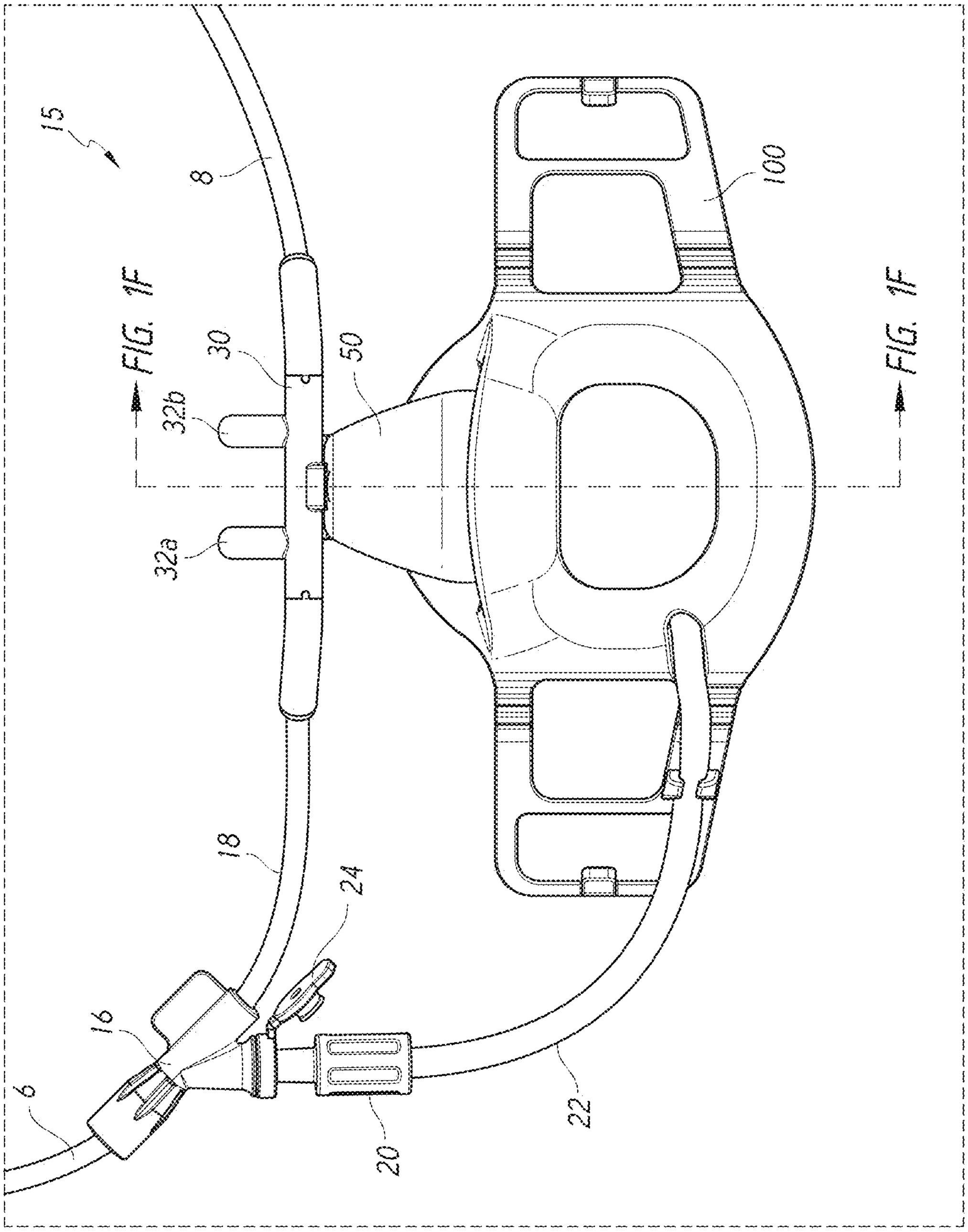

FIG. 1A illustrates a bite block assembly 1. FIG. 1D illustrates an enlarged view of a nasal cannula assembly 15 and a bite block 100, and FIGS. 1B-1C illustrate enlarged views of portions of gas delivery tube 2, 6, gas sampling tubes 4, 8, and couplers and connectors connected to portions thereof. Bite block 100 can be utilized to facilitate insertion of an endoscopic tube into a subject's mouth and inhibit (for example, prevent) the subject from biting down on the endoscopic tube. As discussed further below, bite block 100 can include a main body and a mouthpiece extending outward from the main body, and such mouthpiece can include a main channel that allows such endoscopic tube to be inserted into the subject's mouth during a procedure and, at the same time, prevent the subject's mouth from closing on the endoscopic tube, thereby avoiding damage to the tube and/or interference with the procedure. Such main body of the bite block can rest outside the subject's mouth when the mouthpiece is positioned in the mouth, and, in some implementations, can be secured to the subject's head (for example, with a strap as discussed below).

As discussed further below, a nasal cannula assembly 15 can be utilized alongside the bite block 100 in order to: deliver gases to one or more of the subject's nostrils; and/or collect exhaled gases from one or more of the nostrils for sampling. With reference to at least FIGS. 1D-1E, the nasal cannula assembly 15 can include a gas delivery tube 18 connected to a first portion (for example, a first end) of a nasal cannula manifold 30, prongs 32*a*, 32*b* for delivering gases (for example, oxygen) and/or collecting gases exhaled from the subject's nostrils, and a gas sampling tube 8 connected to a second portion (for example, a second end) of the nasal cannula manifold 30. Bite block 100 can be utilized for oral delivery of gases (for example, oxygen) to the subject's mouth and/or for collecting orally exhaled gases from the subject's mouth. The nasal cannula assembly 15 and the bite block 100 can interact with and/or engage one another in order to accomplish oral and/or nasal gas delivery and/or exhaled gas sampling. For example, in some implementations, bite block assembly 1 includes a branched connector 16 that allows gases from a gas source to be split between tube 18 (for delivery to the nasal cannula manifold 30) and a gas delivery tube 22 that can be connected to a portion of the bite block 100 for delivery of such gases into the subject's mouth. As another example, in some implementations, a scoop 50 (which can be included in nasal cannula assembly 15) connected to the nasal cannula manifold 30 can be utilized to guide orally exhaled gases from a sampling channel of bite block 100 (such as sampling channel 114 discussed further below) to the nasal cannula manifold 30 for sampling. As discussed further below, the scoop 50 can be sized and/or shaped to fit within a region formed by a pocket wall extending outward from and along a portion of the main body of the bite block 100 around the sampling channel of bite block 100. Such pocket wall can be wall 112 described further below.

Figure 1E:
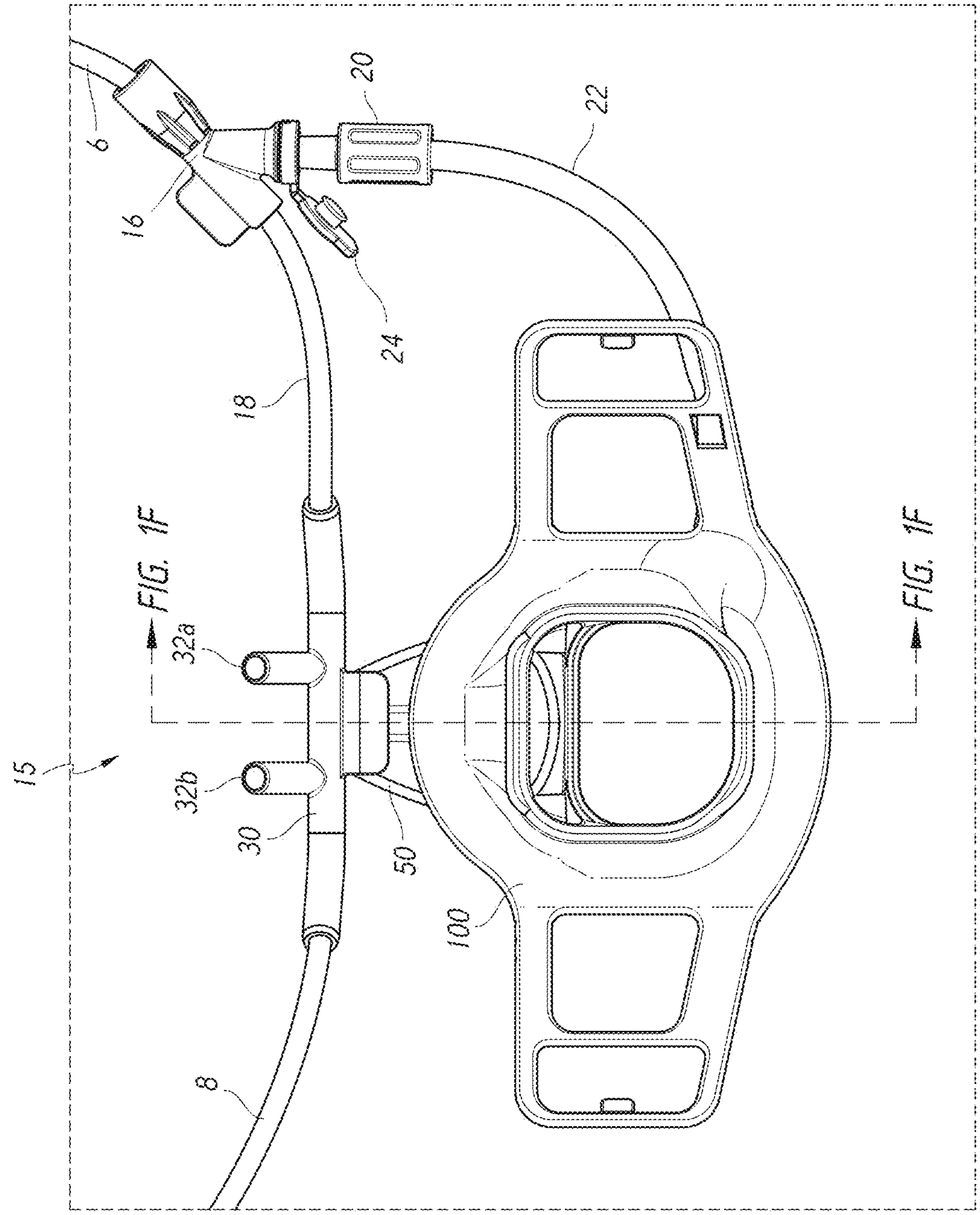
FIG. 1E illustrates a back view of the portion of the bite block assembly shown FIG. 1D in accordance with aspects of this disclosure.
Figure 2:
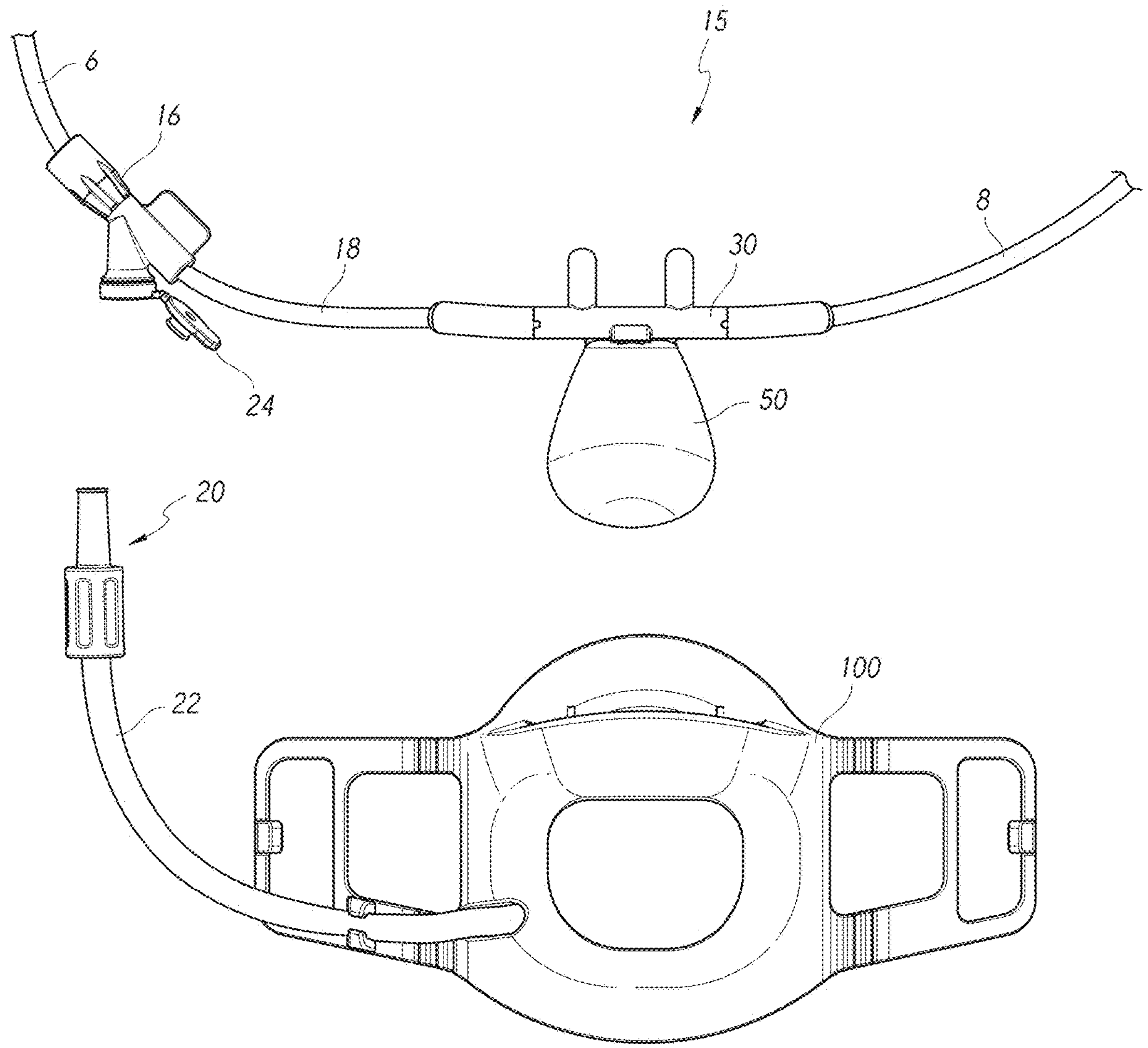
FIG. 2 illustrates portions of the bite block assembly of FIG. 1A separated from one another in accordance with aspects of this disclosure.
Figure 3:
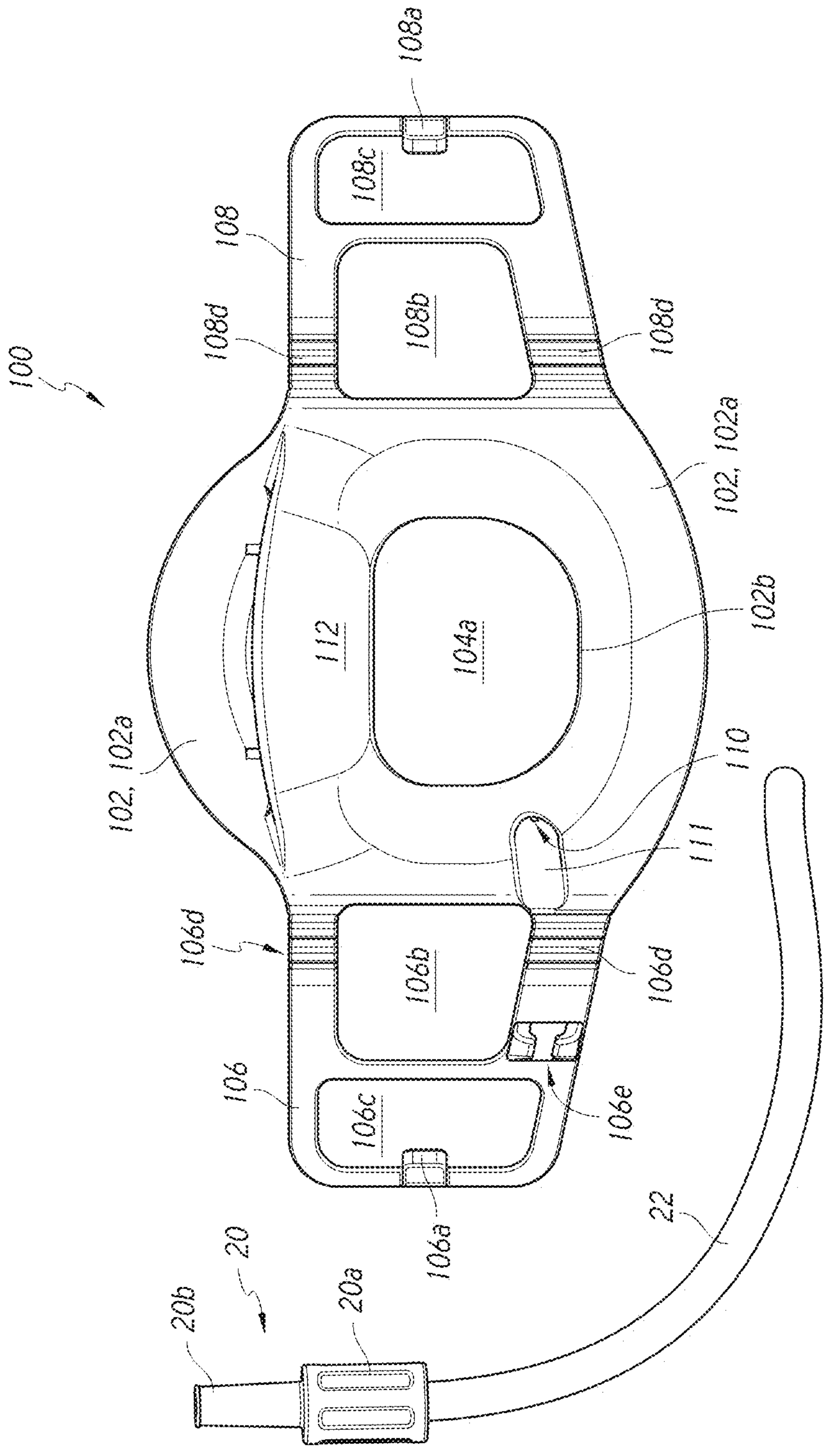
FIG. 3 illustrates a bite block and gas delivery tube of the bite block assembly of FIG. 1A in accordance with aspects of this disclosure.

Advantageously, the nasal cannula assembly 15 and the bite block 100 can be removable from one another, thereby allowing the nasal cannula assembly 15 to continue to be utilized (for gas delivery and/or exhaled gas sampling) before, during, and after the bite block 100 is positioned within the subject's mouth. For example, in some implementations, the scoop 50 does not secure (for example, connect) to the bite block 100, but rather, rests and/or is otherwise positioned in a space defined by a pocket wall (for example, wall 112) of bite block 100. In some implementations, a connector 20 (which can be permanently or removably connected to tube 22) can removably secure within a branch 16*c* of branched connector 16, as shown in FIGS. 1D-1E and FIG. 2. As also discussed further below, when such branch 16*c* (see FIGS. 6A-6B) is closed and/or not connected to connector 20, such branch 16*c* can be manually closed with a cap 24 so that delivery gases are only directed toward branch 16*b*, tube 18, and the nasal cannula manifold 30. With reference to FIG. 3, in some implementations, connector 20 has a body 20*a* and a tapered end 20*b* connected to body 20*a*, and tapered end 20*b* is sized and/or shaped to fit within (for example, via a friction fit arrangement) branch 16*c* of branched connector 16 (see FIG. 6A).

With reference to FIG. 2, nasal cannula assembly 15 can include a gas delivery tube 18, a nasal cannula manifold 30, a gas sampling tube 8, and/or a branched connector 16 as discussed above. With reference to FIG. 1B, in some implementations, nasal cannula assembly 15 additionally includes a coupler 10 that can retain tubes 6, 8. Coupler 10 can have a rounded (for example, cylindrical) shape and can be configured to receive tubes 6, 8. In some implementations, nasal cannula assembly 15 includes a coupler 12 that joins gas delivery tube 6 with another gas delivery tube 2 and/or that joins gas sampling tube 8 with gas sampling tube 4. In some implementations, gas delivery tubes 6 and 2 are different, for example, have different cross-sections. In some implementations, gas sampling tubes 8 and 4 are different, for example, have different cross-sections. With reference to FIG. 1C, a connector 2*a* can be located at an end of tube 2. Connector 2*a* can be connected to a portion of a gas source (for example, an oxygen gas source). As also shown, a connector 14 can be positioned on an end of tube 4 for connecting to a monitoring device. In some implementations, connector 14 includes moisture wicking structure configured to wick moisture away from the subject's exhaled gases and/or includes a hydrophobic bacteria filter.

Figure 4A:
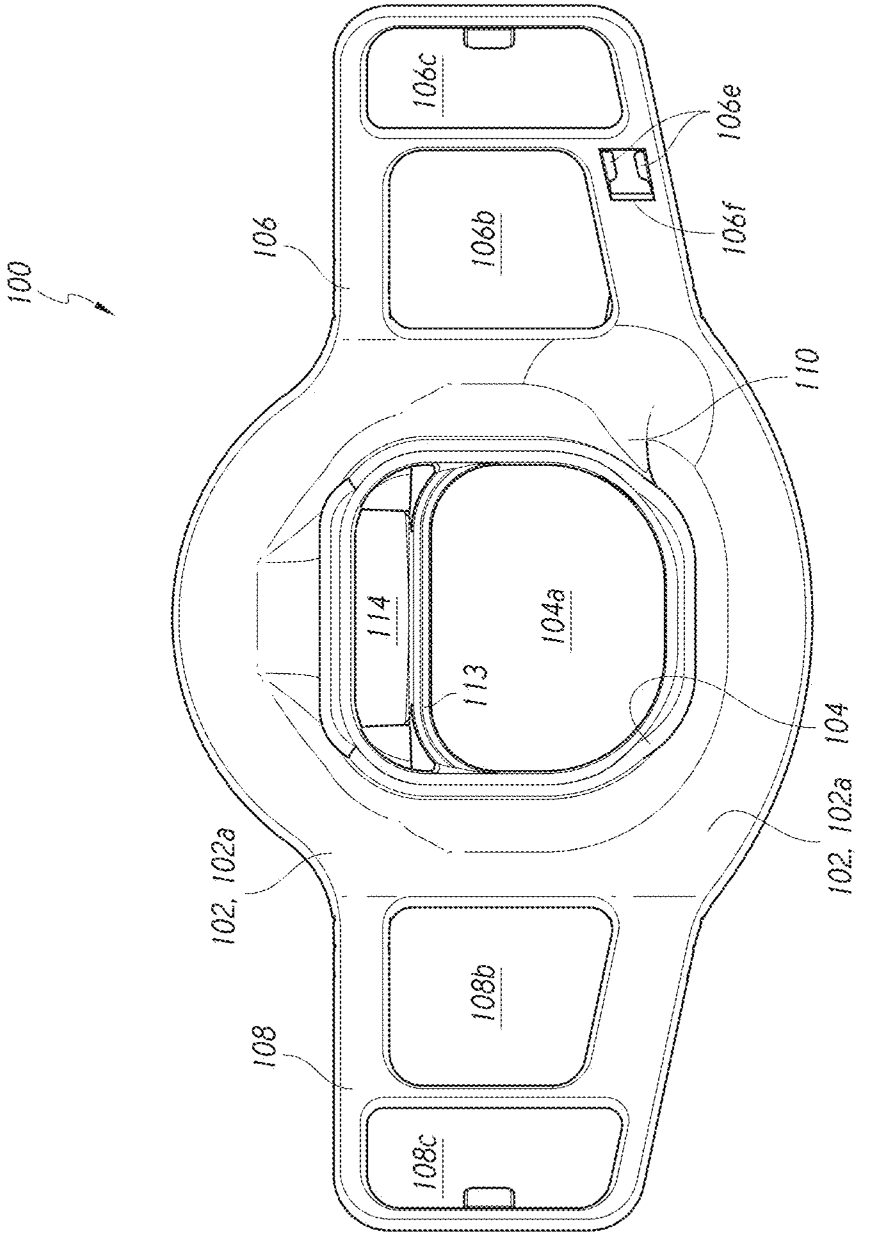
FIG. 4A illustrates a back view of the bite block of FIG. 3 in accordance with aspects of this disclosure.
Figure 4C:
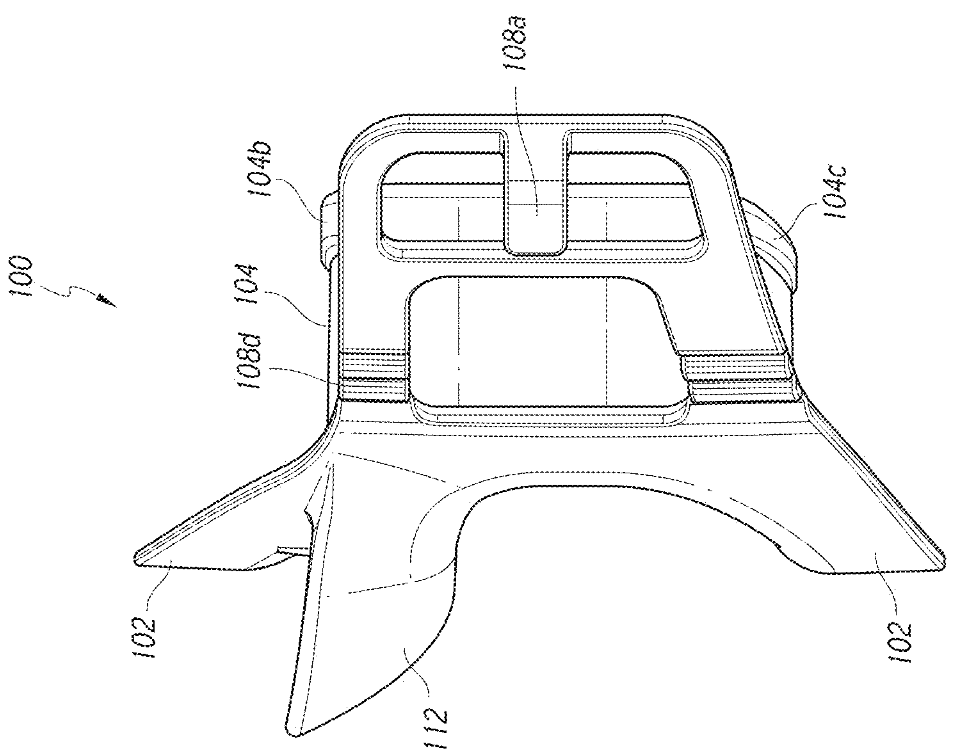
FIGS. 4B-4C illustrate side views of the bite block of FIG. 3 in accordance with aspects of this disclosure.
Figure 4B:
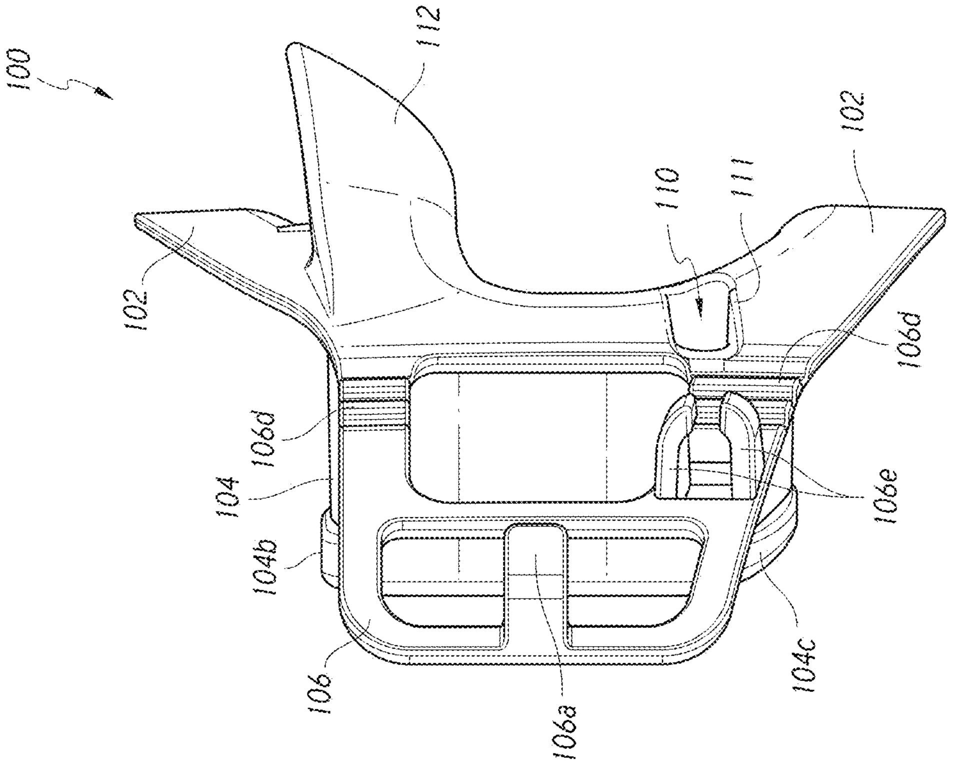
Figure 4D:
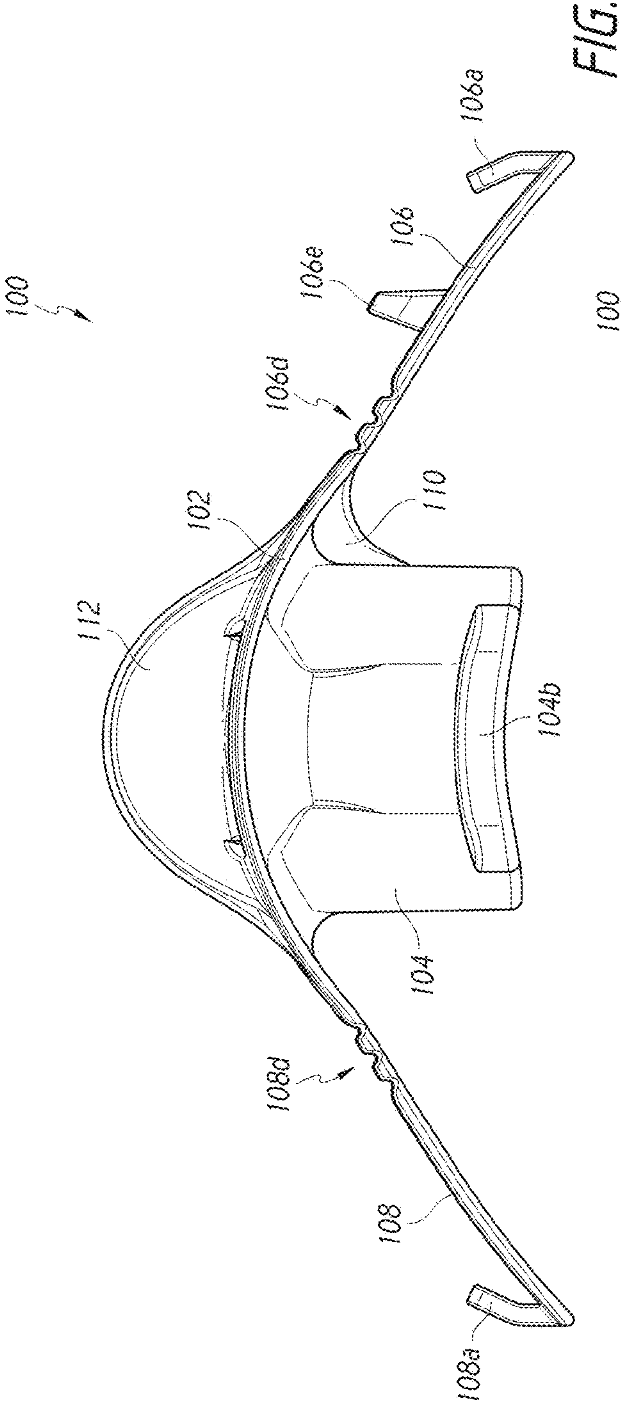
FIGS. 4D-4E illustrate top and bottom views of the bite block of FIG. 3 in accordance with aspects of this disclosure.
Figure 4E:
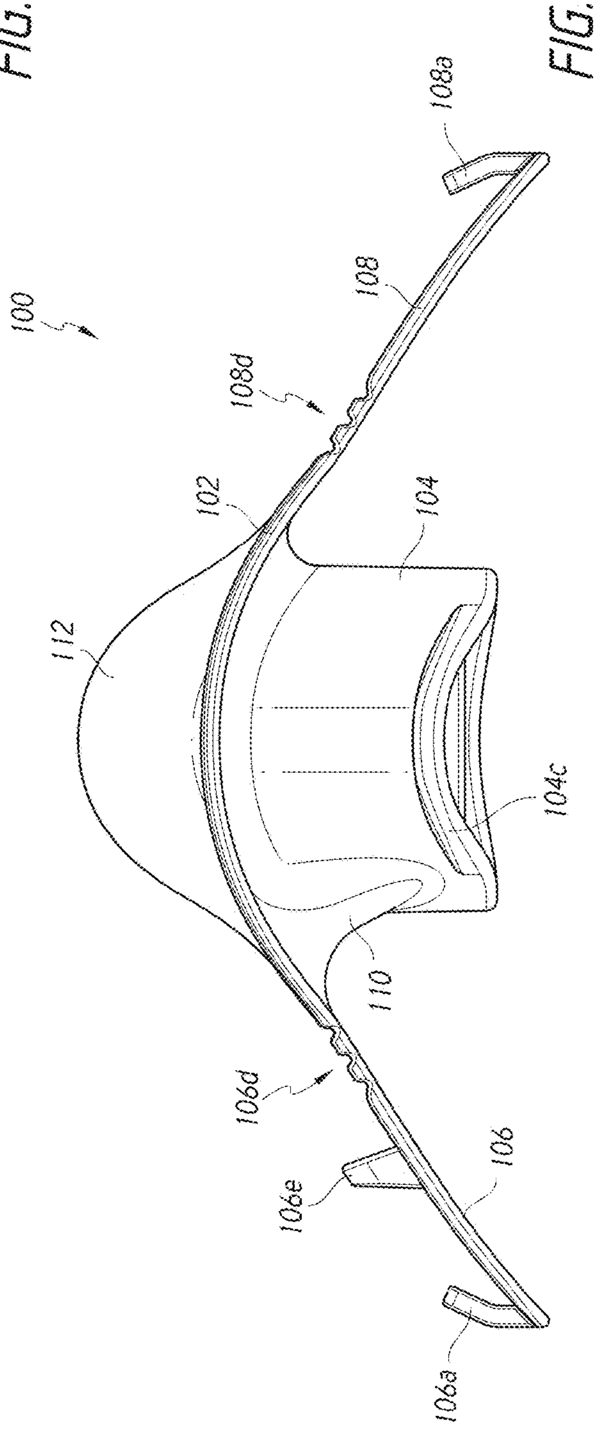
Figure 4F:
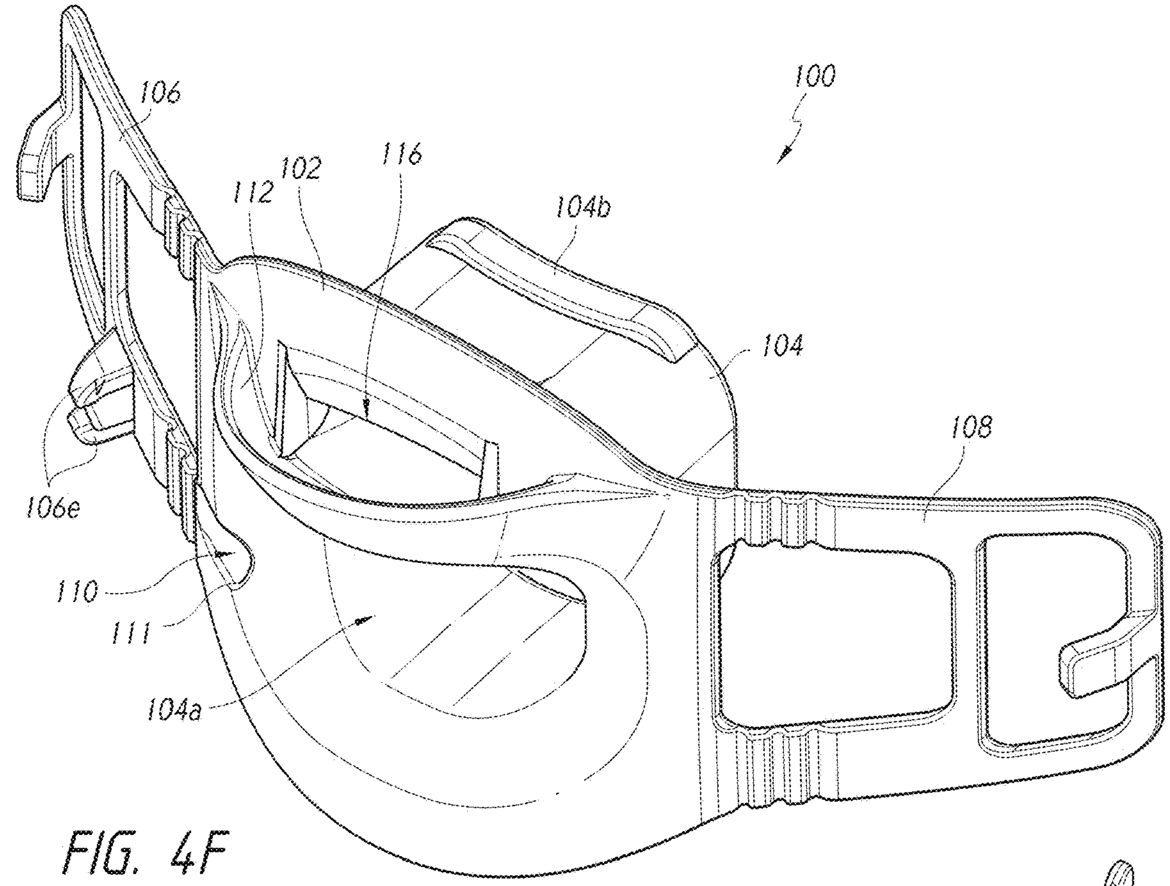
FIGS. 4F-4J illustrate perspective views of the bite block of FIG. 3 in accordance with aspects of this disclosure.
Figure 4G:
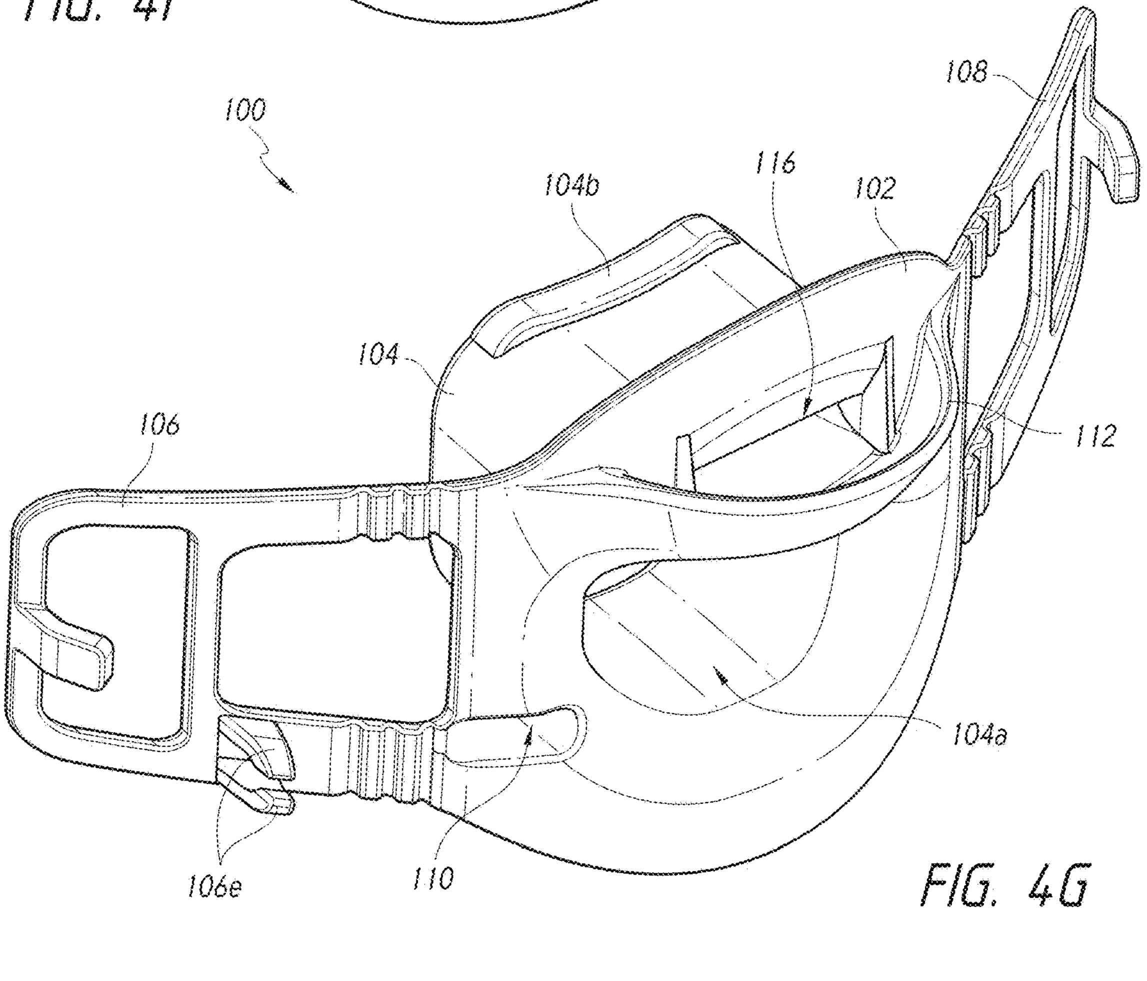
Figure 4H:
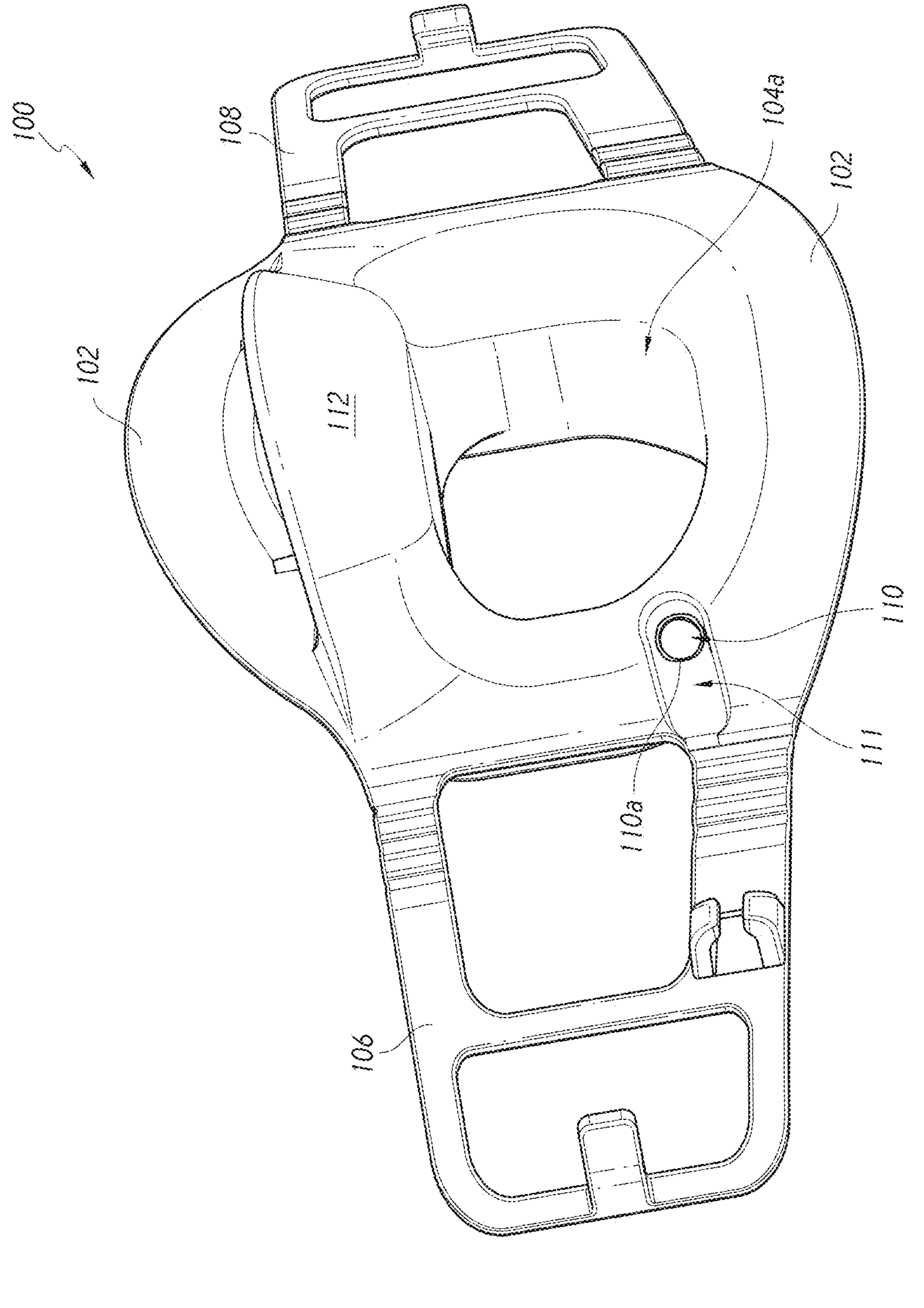

FIG. 3 illustrates a front view of bite block 100 and gas delivery tube 22 disconnected from one another. As discussed further below, in some implementations, gas delivery tube 22 is permanently secured to bite block 100 (for example, within recess 111 and/or gas delivery channel 110). With reference to FIGS. 3-4J, bite block 100 can include a main body 102 and a mouthpiece 104. Mouthpiece 104 can extend outward from the main body 102, for example, from a first surface (which may also be referred to herein as a "rear surface") of the main body 102 that faces toward the subject when bite block 100 is in use. Main body 102 can include a second surface (which may also be referred to herein as a "front surface") opposite such first surface which faces away from the subject when the mouthpiece 104 is positioned in the subject's mouth. Portions of the main body 102 can rest outside and/or contact portions of the subject's face around the mouth (for example, the subject's lips) and prevent mouthpiece 104 from moving further into the subject's mouth. For example, portions of main body 102 around (for example, above and below) the opening 102*b* (see FIG. 3) and/or opening 116 (see FIGS. 4F-4G) can rest outside and/or contact the lips of the subject when mouthpiece 104 is positioned within the subject's mouth. Such portions of main body 102 that rest outside and/or contact the subject's lips when mouthpiece 104 is positioned in the subject's mouth can be an intermediate portion 102*a* discussed below.

FIGS. 3-4J illustrate various views of bite block 100. As mentioned above, bite block 100 can include main body 102 and mouthpiece 104 extending outward form main body 102. Main body 102 can include wings 106, 108 and an intermediate portion 102*a* positioned between wings 106, 108. Wings 106, 108 can extend outward from intermediate portion 102*a* in opposite directions and can be positioned on opposite sides of the subject's mouth when bite block 100 is in use. In some implementations, wings 106, 108 cooperate with a strap 3 (see FIG. 1A) to secure the bite block 100 to the subject's head. For example, strap 3 can include a plurality of holes (see FIG. 1A) configured to receive strap hooks 106*a*, 108*a* extending from wings 106, 108. Strap hooks 106*a*, 108*a* can extend at least partially inward from ends of wings 106, 108 (see FIGS. 4D-4E). Wings 106, 108 can include openings 106*c*, 108*c* that can receive portions of strap 3 to facilitates securement with strap hooks 106*a*, 108*a*. In some implementations, bite block 100 includes flexible hinges 106*d*, 108*d* that can improve flexibility of wings 106, 108, for example, relative to intermediate portion 102*a* of main body 102. Such hinges 106*d*, 108*d* can be defined by reduced cross-section portions on the wings 106, 108, for example, at or near a region where wings 106, 108 connect to intermediate portion 102*a*. In such implementations, such hinges 106*d*, 108*d* may be referred to as living hinges.

In some implementations, bite block 100 includes one or more tube clips configured to secure a portion of gas delivery tube 22. For example, with reference to at least FIGS. 3, 4B, and 4D-4H, bite block 100 can include a tube clip 106*e*. Tube clip 106*e* can include two arms that extend from a portion of main body 102 (for example, from a surface of wing 106). Such two arms can be separated from one another, and free ends of such arms of tube clip 106*e* can be spaced from one another by a gap. Such configuration can allow the two arms to be moved (for example, flexed) away from one another to facilitate positioning of a portion of tube 22 therebetween. Such two arms can be resilient. Accordingly, in some implementations, tube clip 106*e* does not surround an entire cross-section of the tube 22 when tube 22 is secured thereto. With reference to FIG. 4A, in some implementations, an opening 106*f* in wing 106 is positioned adjacent the two arms of tube clip 106*e*. Opening 106*f* can allow the portion of tube 22 secured by tube clip 106*e* to be more easily moved (for example, pushed) out of securement with tube clip 106*e*. In some implementations, bite block 100 only includes one tube clip configured to secure a portion of gas delivery tube 22 (which can be, for example, tube clip 106*e*).

With reference to FIGS. 3, 4A, and 4F-4J, mouthpiece 104 can include a main channel 104*a*. Main channel 104*a* can be defined at least partially by an opening 102*b* in main body 102 (see FIG. 3). For example, opening 102*b* can form a first end of main channel 104*a*. Mouthpiece 104 can have a first end connected to main body 102 and a second, opposite end that terminates a distance away from main body 102 (see FIGS. 4D-4E). Main channel 104*a* can be utilized to allow a tube (for example, an endoscopic tube) to be inserted through bite block 100 and into a subject's mouth (and into other regions of the subject's body) during a procedure. With reference to at least FIGS. 4B-4E, in some implementations, mouthpiece 104 includes protrusions 104*b*, 104*c* that can interact with teeth and/or other portions of the subject's mouth to facilitate proper positioning and/or orientation of bite block 100 when in use. Protrusions 104*b*, 104*c* can extend outward from a portion of (for example, an exterior surface of) mouthpiece 104 and can extend along a portion of a width of mouthpiece 104 (see FIGS. 4D-4E). In some implementations, protrusions 104*b*, 104*c* are positioned at the second ("free") end of mouthpiece 104.

Bite block 100 can include a gas delivery channel to allow gases (for example, oxygen) to be delivered to the subject's mouth when bite block 100 is in use, and such oral gas delivery can be in addition to or as an alternative to gas delivery via the nasal cannula assembly 15 (via the subject's nostrils) discussed elsewhere herein. This is advantageous since many subjects breath via oral inhalation either primarily or in a supplementary manner along with nasal inhalation. With reference to at least FIGS. 3-4B, 4D-4J, bite block 100 can include a gas delivery channel 110. Gas delivery channel 110 can extend through a portion of main body 102 and/or a portion of mouthpiece 104. For example, with reference to FIG. 3, gas delivery channel 110 can extend through a portion of main body 102 proximate to opening 102*b*. FIGS. 4A, 4D-4E, and 4I-4J illustrate an outer portion (which also may be referred to herein as "outer structure") that at least partially defines gas delivery channel 110. As shown in at least FIGS. 4A, 4D-4E, and 4I, gas delivery channel 110 can be at least partially defined along an outer portion of the mouthpiece 104, for example, at a region where mouthpiece joins main body 102. Gas delivery channel 110 can extend transverse relative to opening 102*b* of main body 102 and/or mouthpiece 104. For example, an axis extending through a center of gas delivery channel 110 (see FIG. 4H) can be transverse to an axis extending through a center of mouthpiece 104 and/or an axis extending through opening 102*b* of main body 102. As shown in FIG. 4J, gas delivery channel 110 can terminate inside the mouthpiece 104, for example, inside main channel 104*a*. The opening of the gas delivery channel 110 into main channel 104 can be angled, as shown in FIG. 4J. Accordingly, gas delivery channel 110 can be in fluid communication with main channel 104*a* and can deliver gases (from tube 22) directly into main channel 104*a* for delivery into the subject's oral passage.

As shown in at least FIGS. 3, 4B, and 4F-4H, main body 102 can include a recess 111. Recess 111 can be recessed from a surface (for example, a "front surface") of main body 102 opposite a surface of main body 102 from which mouthpiece 104 extends. Recess 111 can extend to gas delivery channel 110 as shown. Recess 111 can advantageously be sized and/or shaped to receive a portion of tube 22, for example, when tube 22 is connected to bite block 100 (for example, via clip 106*e*) and/or when an end of tube 22 is positioned within at least a portion of gas delivery channel 110. Recess 111 can therefore advantageously allow tube 22 to more easily bend, flex, and/or be positioned in gas delivery channel 110, which can minimize or prevent "kinking" of tube 22 that can interfere with oral gas delivery to the subject. Recess 111 can comprise a smooth and/or rounded surface. Recess 111 can be configured to surround less than an entire cross-section of a portion of tube 22 when secured therewith. For example, recess 111 can be configured to surround less than about ¾ of a cross-section of tube 22 when tube 22 is positioned in recess 111. In some implementations, recess 111 (or at least a portion thereof) has a substantially semi-circular cross-section. In some implementations, recess 111 has a first end at gas delivery channel 110 and extends outward from such first end, for example, toward wing 106 and/or tube clip 106*e*. In some implementations, recess 111 is integrally formed with gas delivery channel 110.

Gas delivery channel 110 is defined at least partially by a cross-section that varies, for example, along a length of gas delivery channel 110. For example, gas delivery channel 110 can have a first cross-section for a portion of a length of the channel 110 and a second cross-section for another portion of the length of the channel 110. Such configuration can define a ledge 110*a* (see FIG. 4H). Such ledge 110*a* can aid the positioning, placement, and/or securement of an end of tube 22 in channel 110. In some implementations, gas delivery channel 110 has a first circular cross-section for a portion of the length of channel 110 and a second circular cross-section for another portion of the length of channel 110, thereby defining a circular ledge 110*a*. In some implementations, an annular ring structure is positioned within gas delivery channel 110, and one end of such annular ring structure can define the ledge 110*a*.

Figure 1F:
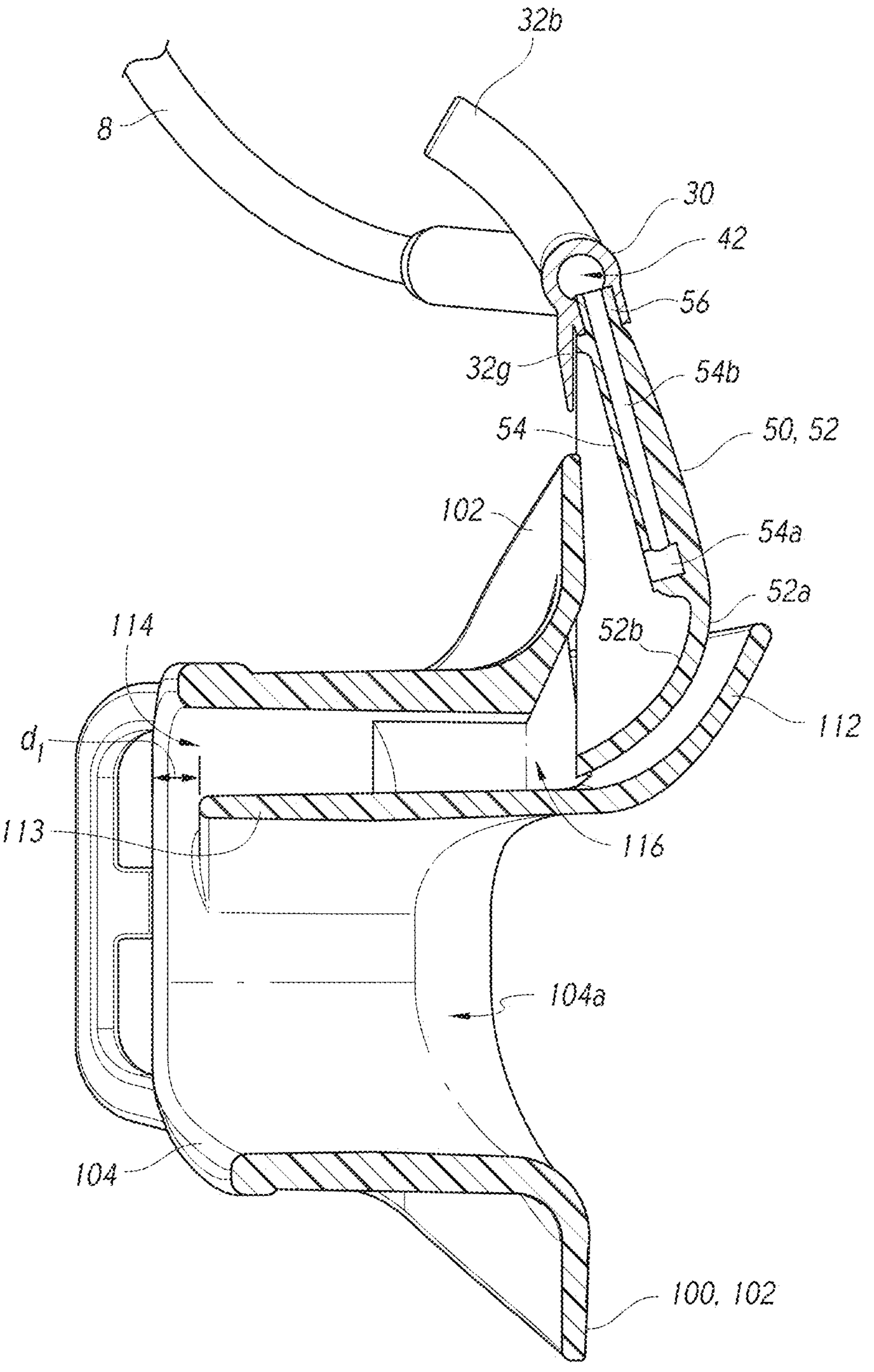
FIG. 1F illustrates a cross-section taken through a portion of the bite block assembly shown FIGS. 1D-1E in accordance with aspects of this disclosure.
Figure 4I:
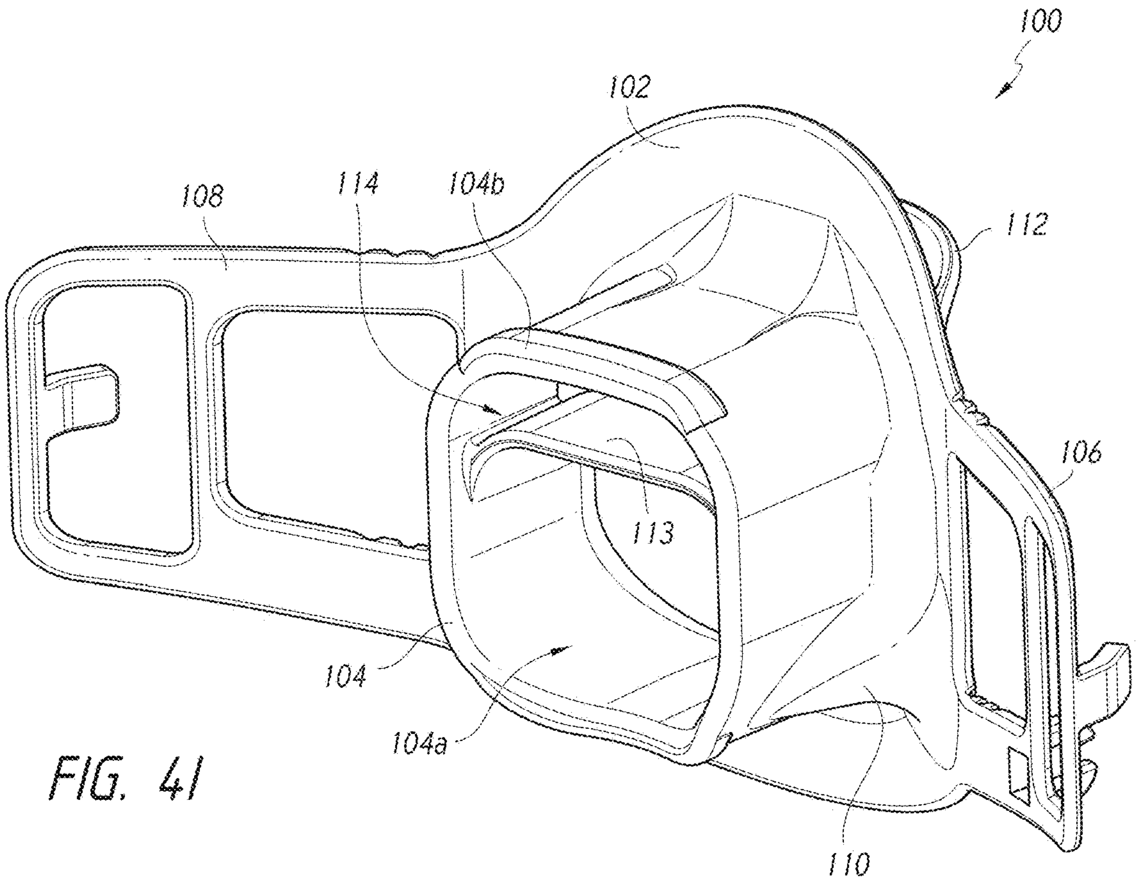
Figure 4J:
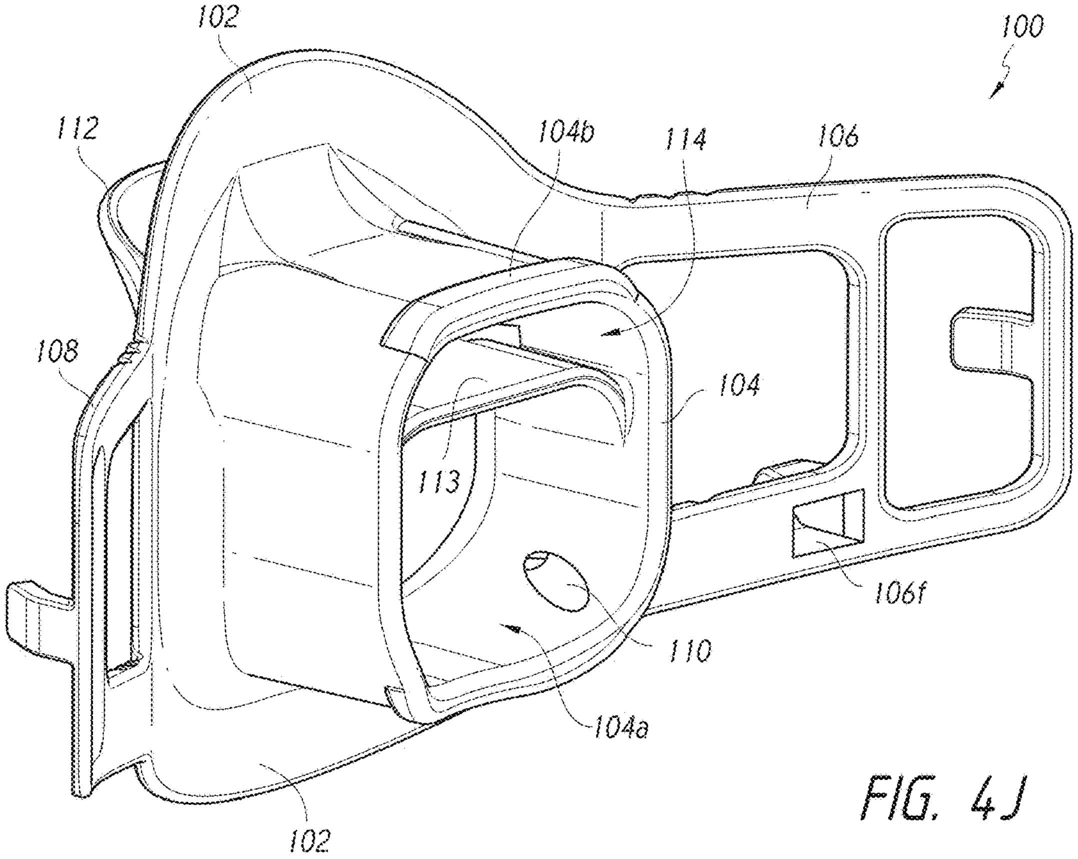

With reference to at least FIGS. 4A and 4I-4J, mouthpiece 104 can include a sampling channel 114 for collecting orally exhaled gases from a subject's mouth when bite block 100 is in use. Bite block 100 (for example, mouthpiece 104) can include a wall 113 (which may be referred to as an "inner wall") that can separate sampling channel 114 from main channel 104*a*. FIG. 1F illustrates a cross-section taken through bite block 100 as well as nasal cannula assembly 15. In some implementations, such as that shown in FIG. 1F, inner wall 113 does not extend beyond an outer end of mouthpiece 104, and an end of inner wall 113 is spaced inward from the outer end of mouthpiece 104 by a distance $d_1$. With reference to FIGS. 1F and 4F-4G, main body 102 can include an opening 116 that is in fluid communication with sampling channel 114. Opening 116 can be positioned adjacent (for example, above) opening 102*b* of main body 102 (see FIGS. 4F-4G).

With reference to at least FIGS. 3 and 4B-4H, bite block 100 can include a wall 112 (which may also be referred to as a "pocket wall") extending outward from a portion of main body 102 and around opening 116 (for example, from a surface of main body 102 that faces away from the subject when bite block 100 is in use). Wall 112 can extend outward from main body 102 and adjacent to opening 102*b* (see FIG. 3). Wall 112 can extend around an entire width of opening 116, where such "width" of opening 116 extends in right and left directions in the view of FIG. 3. Wall 112 can at least partially define (for example, along with a portion of main body 102) a space that is sized and/or shaped to receive a portion of scoop 50 of nasal cannula assembly 15. For example, with reference to at least FIGS. 1D-1F, a portion (for example, an end) of scoop 50 can be received within a space defined by wall 112 and main body 102 around opening 116. Advantageously, orally exhaled gases can be directed by sampling channel 114 through opening 116 and towards scoop 50 when scoop 50 is positioned between wall 112 and opening 116. The collection of such exhaled gases by scoop 50 and nasal cannula assembly 15 is described further below.

Figure 5:
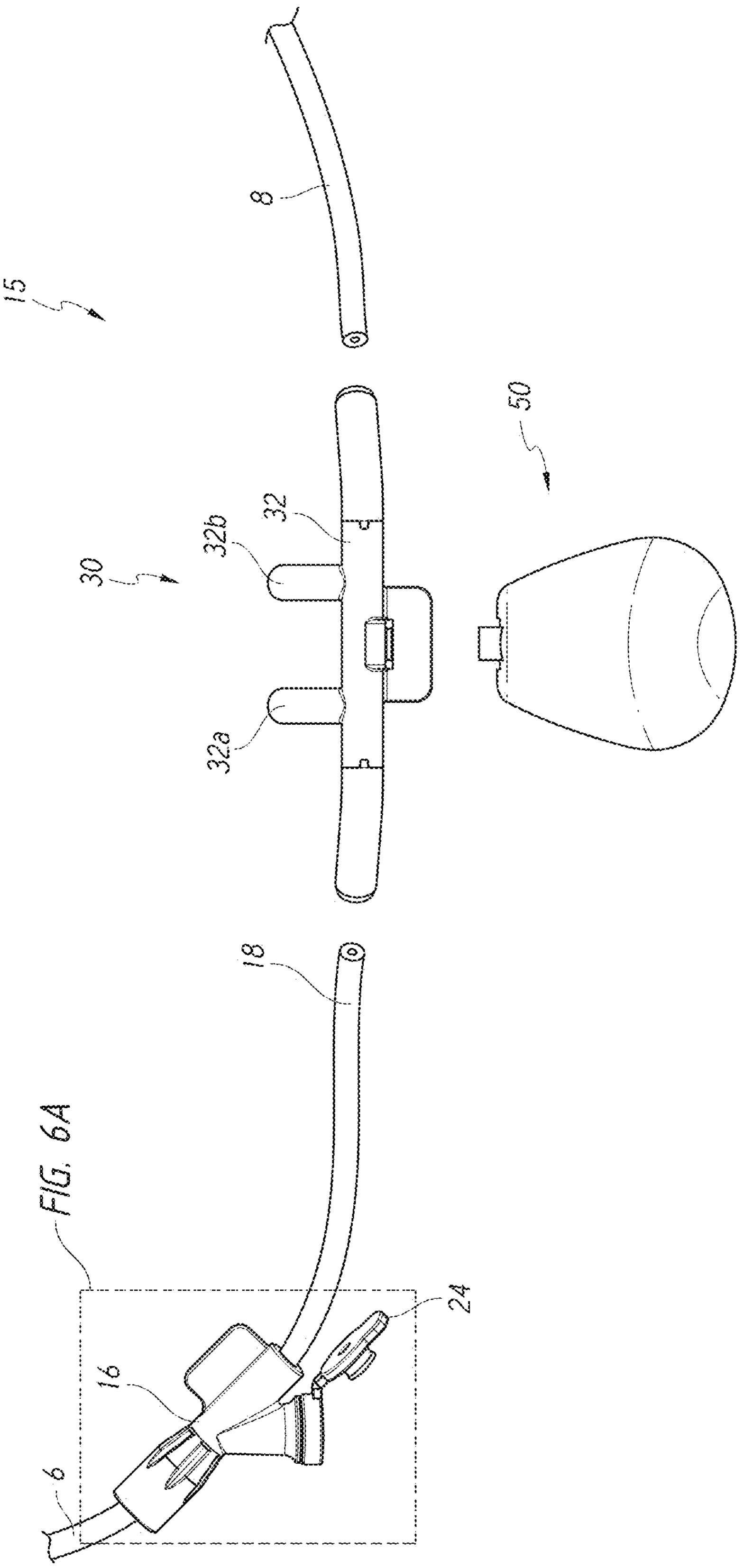
FIG. 5 illustrates a partially exploded view of a nasal cannula assembly of the bite block assembly of FIG. 1A in accordance with aspects of this disclosure.

FIGS. 1D-1F illustrate nasal cannula assembly 15 engaged with bite block 100 and FIG. 2 illustrates nasal cannula assembly 15 separated from bite block 100 (and separated from tube 22 and connector 20). FIG. 5 illustrates a partially exploded view of nasal cannula assembly 15. Although FIG. 5 does not illustrate tubes 2, 4, couplers 10, 12, and connectors 2*a*, 14, any or all of such components (which are described above) can form part of nasal cannula assembly 15, and/or nasal cannula assembly 15 can include additional or alternative components. As shown in FIG. 5, nasal cannula assembly 15 can include gas delivery tubes 6, 18, a branched connector 16, a closable cap 24 connected to the branched connector 16, a nasal cannula manifold 30 (which can include nasal prongs 32*a*, 32*b*), a scoop 50, and a gas sampling tube 8.

Figure 6B:
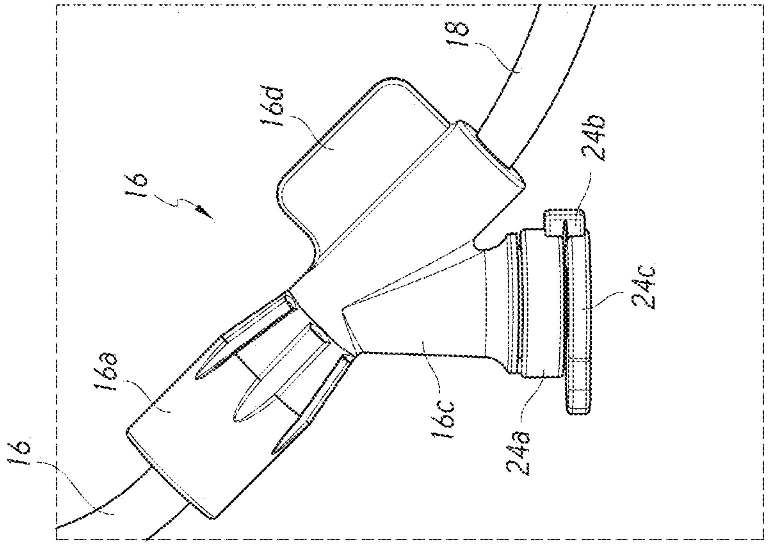
FIGS. 6A-6B illustrate enlarged views of a branched connector of the nasal cannula assembly of FIG. 5 in accordance with aspects of this disclosure.
Figure 6A:
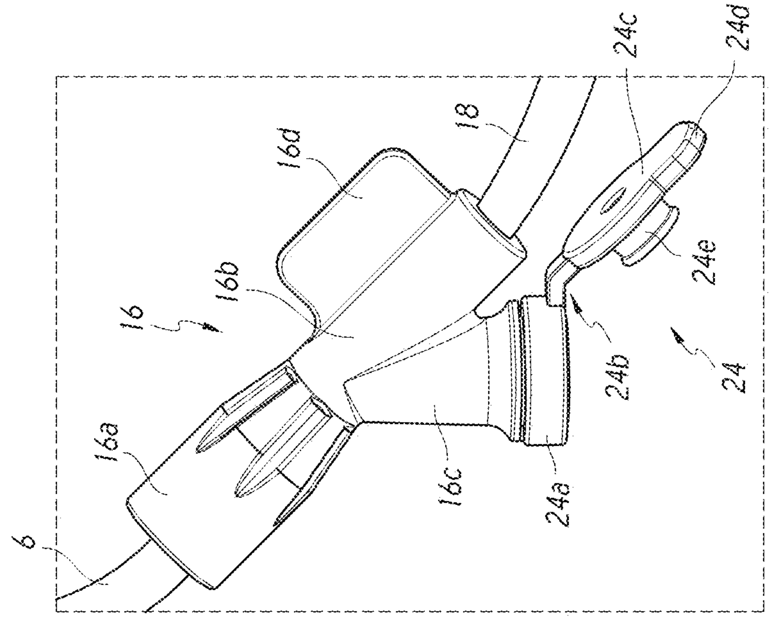

FIG. 6A illustrates an enlarged view of branched connector 16 and cap 24, and also illustrates portions of tubes 6, 18. Branched connector 16 can include a first branch 16*a*, a second branch 16*b*, and a third branch 16*c*. Branch 16*a* can be permanently or removably connected to tube 6. Branch 16*b* can be permanently or removably connected to tube 18. In some embodiments, branched connector 16 includes a flange 16*d* (for example, extending outward and/or along branch 16*b*) that can aid a user in handling branched connector 16. Branch 16*c* can be configured to removably connect to gas delivery tube 22, for example, via connector 20 secured to an end of tube 22. With reference to FIG. 3, branch 16*c* can be configured to receive a tapered end 20*b* of connector 20 (see FIGS. 1D-1E and 3). The securement between tapered end 20*b* and branch 16*c* can be a friction fit engagement. Alternatively, in some implementations, connector 20 is configured to secure to branch 16*c* via a snap fit engagement. Connection between connector 20 and branch 16*c* can facilitate fluid communication between tube 22 and tube 6, thereby allowing gases (for example, oxygen) to be delivered by tube 6 and branch 16*c* to tube 22 (and to gas delivery channel 110 in bite block 100). Branch 16*b* can facilitate fluid communication between tube 18 and tube 6. Branched connector 16 can include an interior defined by interiors of branches 16*a*, 16*b*, 16*c*, all of which can be in fluid communication with each other and with tubes 6, 18, and/or 22 when connected therewith.

With continued reference to FIGS. 6A-6B, cap 24 can be secured to a portion of branched connector 16 to enable a fluid flow path through branch 16*c* to be closed, for example, when connector 20 and tube 22 are not connected to branch 16*c*. Cap 24 can include a base 24*a*, a lid 24*c*, and a hinge 24*b*. Base 24*a* can be secured to (for example, around all or a portion of a perimeter of) branch 16*c*. Hinge 24*b* can be positioned between base 24*a* and lid 24*c* and can connect base 24*a* and lid 24*c*. Hinge 24*b* can allow lid 24*c* to move (for example, rotate) relative to base 24*a*. Hinge 24*b* can be a living hinge. In some implementations, cap 24 (for example, base 24*a*) is permanently secured to branched connector 16 (for example, to branch 16*c*). FIG. 6A illustrates cap 24 in an open position where branch 16*c* is in fluid communication with the ambient environment when not connected with tube 22 (via connector 20). In such open position, connector 20 (for example, tapered end 20*b*) can be inserted within branch 16*c*. FIG. 6B illustrates cap 24 in a closed position, where branch 16*c* is not in fluid communication with the ambient environment. With reference to FIG. 6A, in some implementations, cap 24 includes a plug 24*e* sized and/or shaped to fit and/or secure within branch 16*c* (for example, an opening into an interior defined within branch 16*c*). Such connection of plug 24*e* within branch 16*c* can be a friction fit arrangement, for example. In some implementations, cap 24 includes a handle 24*d* (which may be referred to as a "handle portion") that can allow a user to grip and/or move (for example, rotate) lid 24*c* and move cap 24 between the closed and open positions.

FIGS. 7A-7D illustrate various views of scoop 50. Scoop 50 can include a body 52 having a first surface 52*a* and a second surface 52*b* opposite the first surface 52*a*. The first surface 52*a* (which may be referred to as an "outer" or "exterior" surface) can face at least partially away from the subject when nasal cannula assembly 15 is in use and the second surface 52*b* (which may be referred to as an "inner" or "interior" surface) can face at least partially toward the subject when nasal cannula assembly 15 is in use. When nasal cannula assembly 15 is used with bite block 100, at least a portion of inner surface 52*b* can face in a direction toward opening 116 and sampling channel 114 of bite block 100 (see, for example, FIG. 1F). In some implementations, such as that shown in the figures, body 52 of scoop 50 has a basin shape. For example, exterior surface 52*a* can have a convex shape, interior surface 52*b* can have a concave shape, and body 52 can have an edge surface 52*c* extending along a juncture of surfaces 52*a*, 52*b* and/or between surfaces 52*a*, 52*b*. As shown, portions of the interior surface 52*b* can be positioned inward from such edge surface 52*c*. Such configurations can allow scoop 50 to better receive and direct exhaled gases from sampling channel 114 and opening 116 of bite block 100.

Figure 7D:
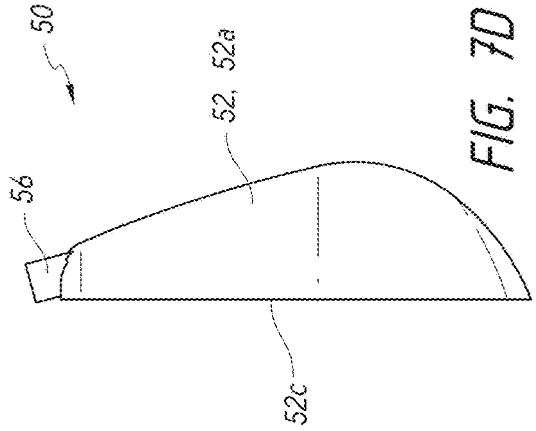
FIGS. 7A-7D illustrate enlarged views of a scoop of the nasal cannula assembly of FIG. 5 in accordance with aspects of this disclosure.
Figure 7B:
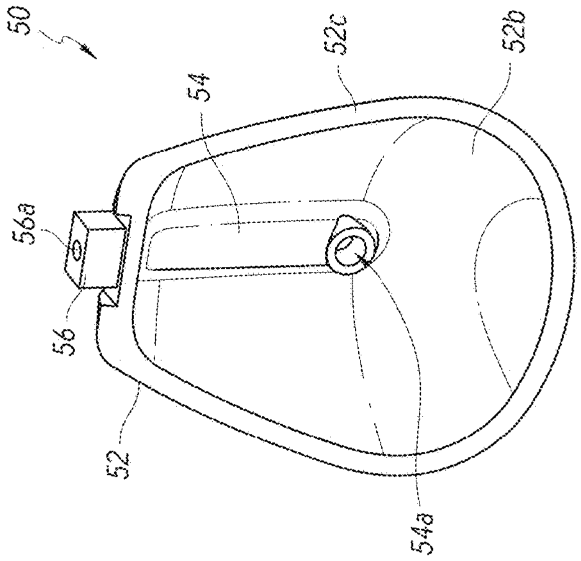
Figure 7C:
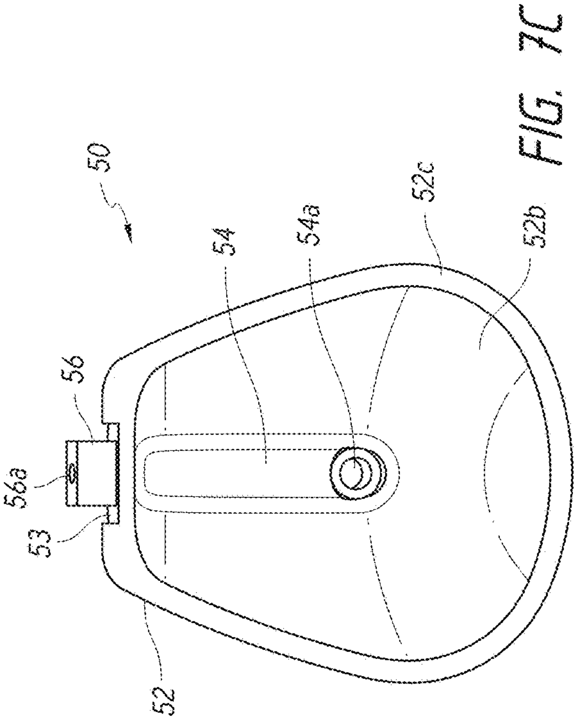
Figure 7A:
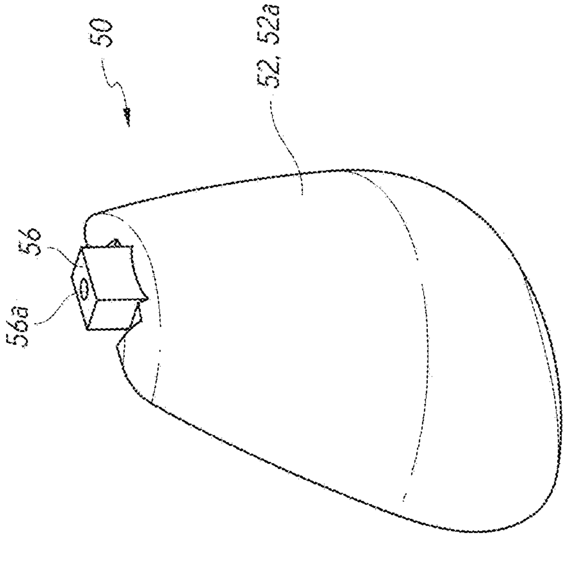

With reference to FIGS. 7B-7C, scoop 50 can include a rib 54 extending outward from and along a portion of surface 52*b*. Rib 54 can extend along a middle of body 52 and/or surface 52*b*. Rib 54 can extend along an axis of symmetry of body 52 and/or scoop 50 (see FIG. 7C). With reference to FIG. 1F, rib 54 can include a first end having an opening into a first fluid passage 54*a*. Rib 54 can include a second fluid passage 54*b* in fluid communication with fluid passage 54*a*. Fluid passages 54*a*, 54*b* can be oriented transverse (for example, perpendicular) to one another. Fluid passages 54*a*, 54*b* can receive orally exhaled gases from opening 116 and sampling channel 114 of bite block 100, which can be guided (at least partially) by body 52 of scoop 50.

Scoop 50 can be configured to connect to nasal cannula manifold 30. In some implementations, scoop 50 includes a connector 56 configured to connect to a portion of nasal cannula manifold 30 (for example, to connector 32*e* of nasal cannula manifold 30 shown in at least FIG. 8A). Connector 56 can include an opening 56*a* and can include a fluid passage in fluid communication with fluid passages 54*b*, 54*a* of rib 54 (see FIG. 1F). In some implementations, scoop 50 includes a notch 53 in body 52 that includes a surface from which connector 56 extends. In some implementations, such notch 53 is sized and/or shaped to accommodate a portion of connector 32*e* of nasal cannula manifold 30 shown in at least FIG. 8A.

Figure 8B:
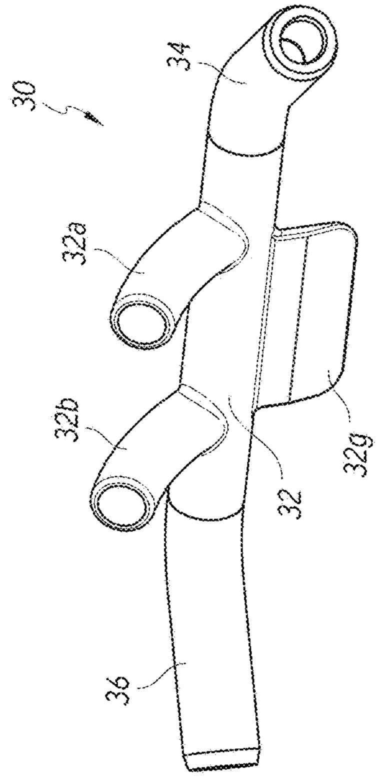
FIGS. 8A-8C illustrate enlarged views of a nasal cannula manifold of the nasal cannula assembly of FIG. 5 in accordance with aspects of this disclosure.
Figure 8A:
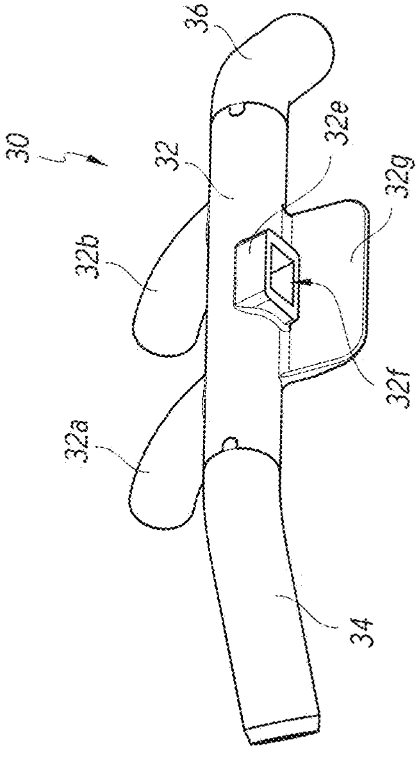
Figure 8C:
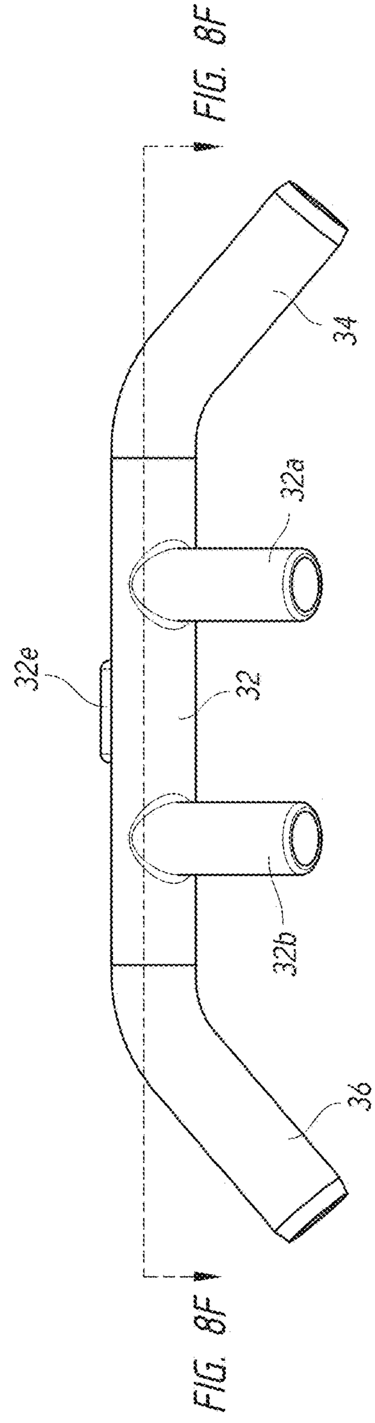
Figure 8D:
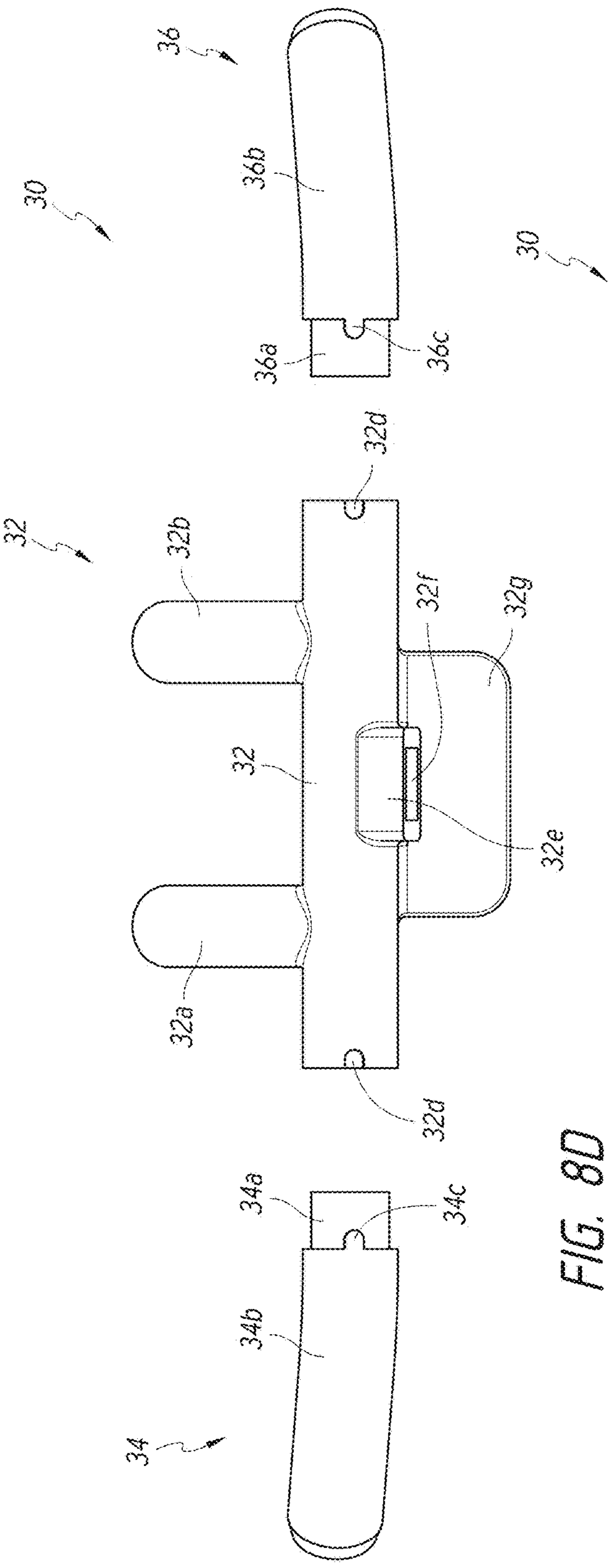
FIGS. 8D-8E illustrate exploded views of the nasal cannula manifold of FIGS. 8A-8C in accordance with aspects of this disclosure.
Figure 8E:
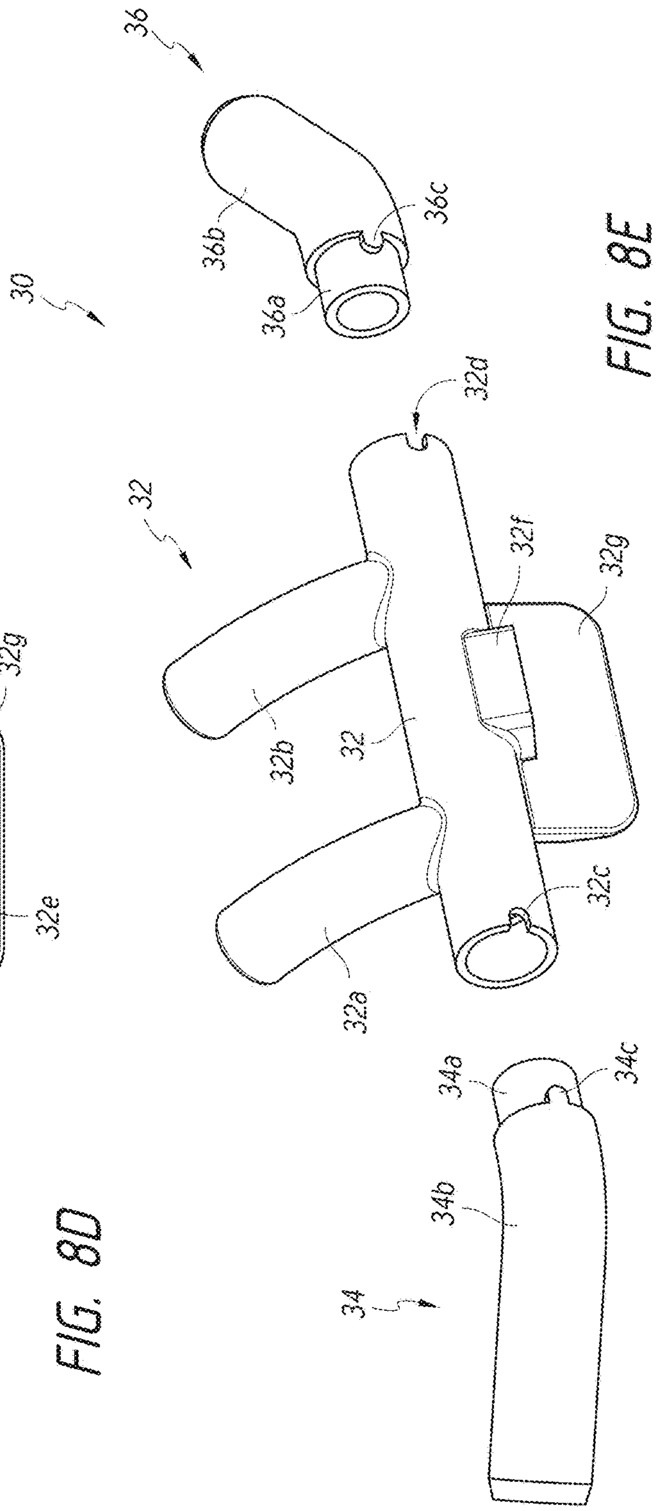

FIGS. 8A-8C illustrate enlarged views of nasal cannula manifold 30. Nasal cannula manifold 30 can include a body 32 (which may be referred to as a "manifold body"), nasal prongs 32*a*, 32*b* spaced from one another and extending outward from body 32, and arms 34, 36. Arms 34, 36 can include a bend, which may also be referred to as a "bent portion" (see FIG. 8C). Such bend can form an angle between about 0 degrees and about 90 degrees, for example, about 45 degrees. Arms 34, 36 can be permanently or removably secured to body 32. In some implementations, arms 34, 36 are integral with body 32. FIGS. 8A-8C illustrate arms 34, 36 connected to body 32, whereas FIGS. 8D-8E illustrate arms 34, 36 separated from body 32. With reference to FIGS. 8D-8E, body 32 can include slots 32*d* (for example, near or at ends of body 32) that are configured to receive and/or secure to protrusions 34*c*, 36*c* on ends of arms 34, 36. In some implementations, arms 34, 36 include a first portion 34*a*, 36*a* and a second portion 34*b*, 36*b*, and the first portions 34*a*, 36*a* have a different (for example, smaller) cross-section than the second portion 34*b*, 36*b*. Such configuration can allow portions 34*a*, 36*a* to be received and/or secured within ends of body 32. Interaction between slots 32*d* and protrusions 34*c*, 36*c* can act to position and/or secure arms 34, 36 with respect to body 32.

As shown in FIGS. 8A-8E, nasal cannula manifold 30 can include a connector 32*e* extending outward from body 32 and configured to connect to connector 56 of scoop 50. Connector 32*e* can include an opening 32*f* that allows connector 56 of scoop 50 to be received and/or secured within connector 32*e*. Connector 32*e* can thereby facilitate fluid communication between fluid passages 54*a*, 54*b* of rib 54 of scoop 50 and an interior portion of the nasal cannula manifold 30.

In some implementations, nasal cannula manifold 30 includes a flange 32*g* extending outward from body 32 and adjacent to connector 32*e*. Flange 32*g* can act to position and/or at least partially secure scoop 50 relative to nasal cannula manifold 30, for example, as shown in FIGS. 1A-2. Flange 32*g* can extend outward from body 32 further than the connector 32*e*. Flange 32*g* can inhibit scoop 50 from moving (for example, pivoting) when connector 56 is positioned within connector 32*e*.

Figure 8F:
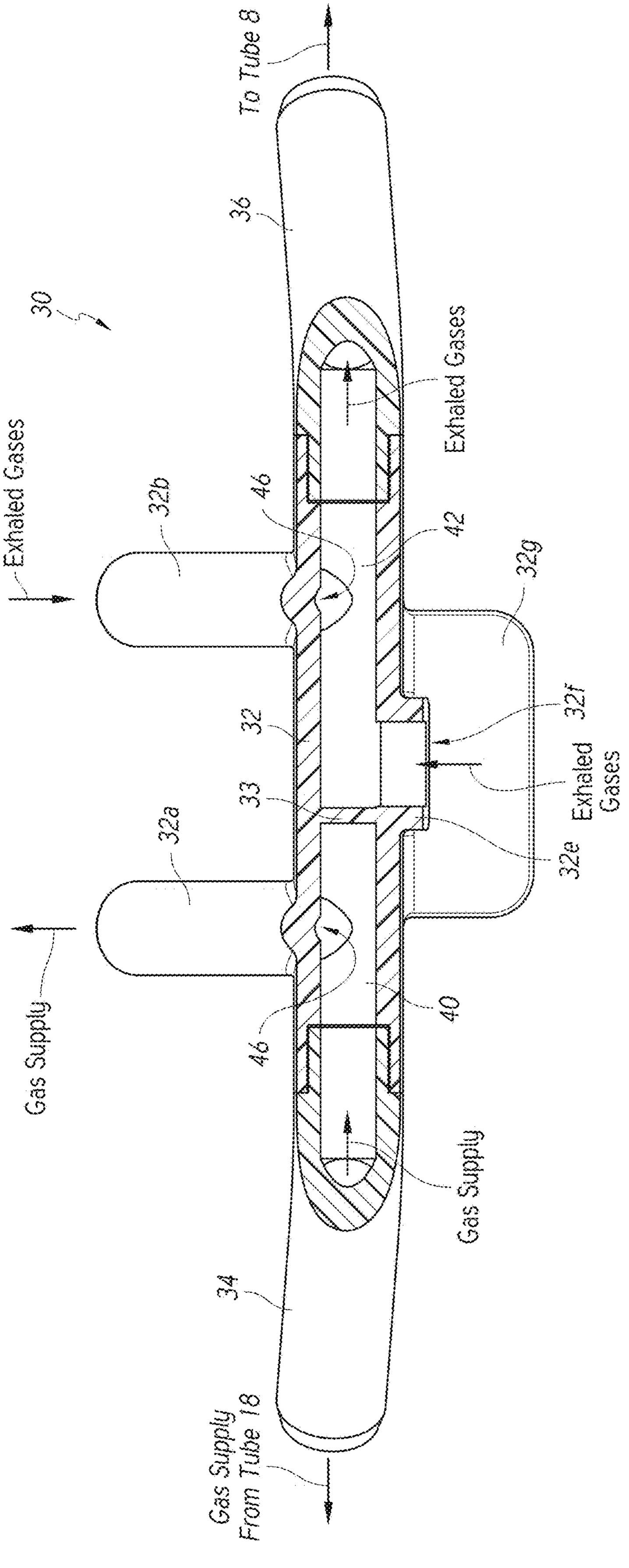
FIG. 8F illustrates a cross-section taken through a portion of the nasal cannula manifold shown in FIG. 8C.

FIG. 8F illustrates a cross-section taken through a portion of nasal cannula manifold 30 shown in FIG. 8C. Nasal cannula manifold 30 can be configured to allow gases (for example, oxygen) to be delivered from a gas supply tube 18 to a subject's nostril or nostrils and to allow gases exhaled from the subject's nostril or nostrils to be directed to gas sampling tube 8. Nasal cannula manifold 30 (for example, body 32) can include an interior portion 40 in fluid communication with gas delivery tube 18 (when connected to nasal cannula manifold 30), arm 34, and/or nasal prong 32*a*. Accordingly, delivery gases can flow through tube 18, arm 34, interior portion 40, and outward towards a nostril of the subject via nasal prong 32*a*. Nasal cannula manifold 30 can include an interior portion 42 that is separated from interior portion 40 by an inner wall 33. Interior portion 40 may be referred to as a first interior portion of nasal cannula manifold 30 and interior portion 42 may be referred to as a second interior portion of nasal cannula manifold 30. Interior portion 42 can be in fluid communication with opening 32*f*, connector 32*e*, nasal prong 32*b*, arm 36, and tube 8 when tube 8 is connected to nasal cannula manifold 30. Nasal prong 32*b* can receive gases exhaled from a nostril of the subject and direct such gases to interior portion 42. In some implementations, nasal cannula manifold 30 includes an inner wall 33, and in such implementations, inner wall 33 can prevent fluid communication between interior portion 40 (and nasal prong 32*a*, arm 34, and/or tube 18) and interior portion 42 (and opening 32*f*, connector 32*e*, nasal prong 32*b*, arm 36, and/or tube 8). Such configuration can reduce mixing of delivered and exhaled gases and allow for accurate measurements based on the exhaled gases.

Figure 9A:
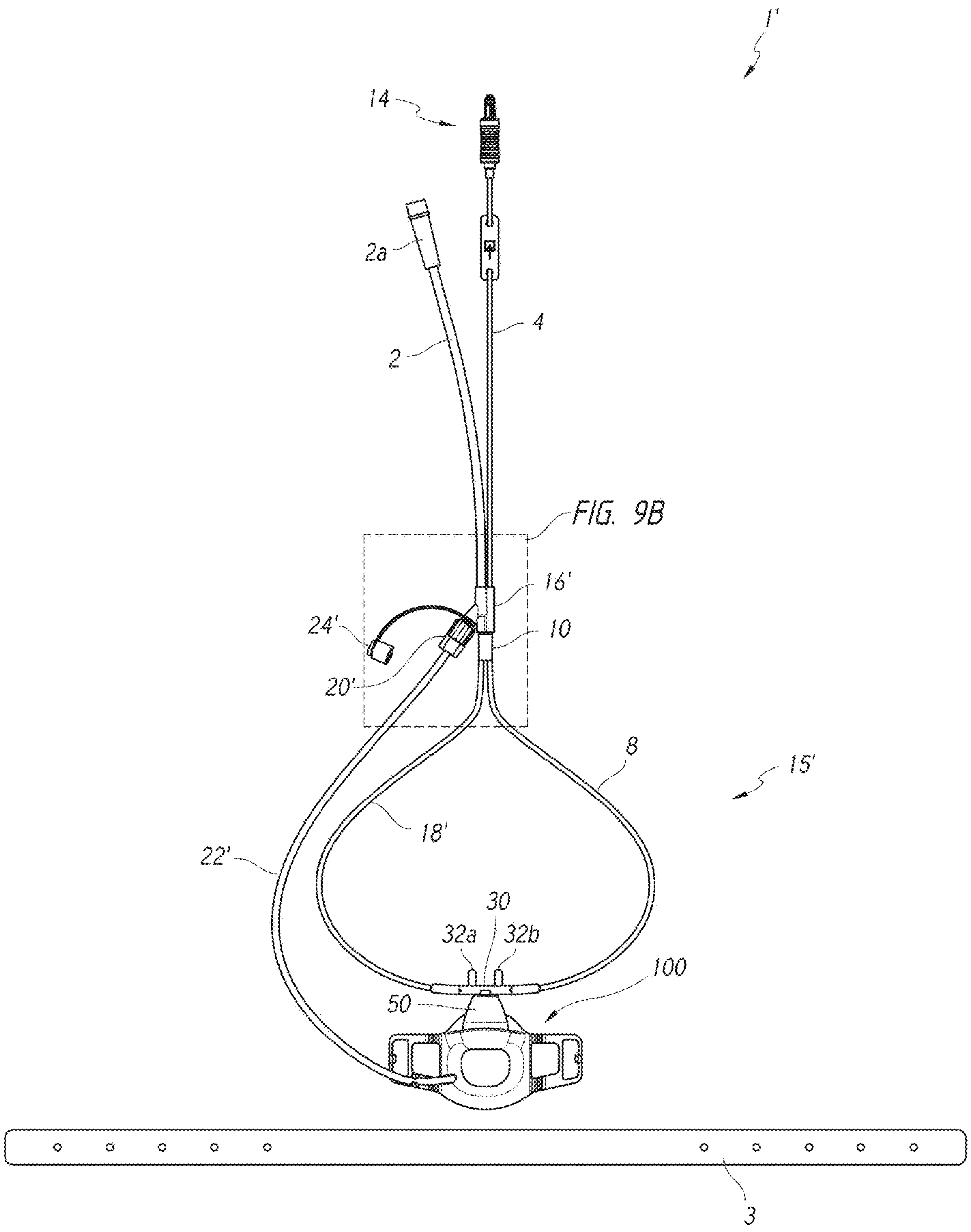
FIG. 9A illustrates a front view of a bite block assembly in accordance with aspects of this disclosure.

FIG. 9A-9D illustrate another implementation of a bite block assembly 1'. Bite block assembly 1' can be similar or identical to bite block assembly 1 in some or many respects. With reference to FIG. 9A, bite block assembly 1' can include bite block 100, strap 3, tubes 2, 4, connectors 2*a*, 14, coupler 10, nasal cannula manifold 30, nasal prongs 32*a*, 32*b*, tube 8, and scoop 50 each of which is described elsewhere herein. Instead of coupler 12 and branched connector 16, bite block assembly 1' can include branched connector 16'. Further, instead of separate tubes 6 and 22 that can supply delivery gas to bite block 100 (and additionally or alternatively to nasal cannula manifold 30), bite block assembly 1' can include a single tube 22' that can supply delivery gas to bite block 100. Assembly 1' can include a nasal cannula assembly 15' that is similar to nasal cannula assembly 15 in some or many respects. Nasal cannula assembly 15' can include a tube 18' that can be similar or identical to tube 18 discussed elsewhere herein. Nasal cannula assembly 15', which can include branched connector 16', coupler 10, tubes 8, 18, nasal cannula manifold 30, prongs 32*a*, 32*b*, tubes 2, 4, and connectors 2*a*, 14, can be separatable from bite block 100 and tube 22', for example, via branched connector 16'.

Similar to branched connector 16, branched connector 16' can allow gases from a gas source to be split between tube 18' (for delivery to the nasal cannula manifold 30) and a gas delivery tube 22' that can be connected to a portion of the bite block 100 for delivery of such gases into the subject's mouth. Branched connector 16' and tubes 18', 22' can be similar or identical to branched connector 16 and tubes 18, 22 described above with reference to nasal cannula assembly 15. As shown, branched connector 16' can be positioned near or above coupler 10 such that branched connector 16' is coupled with gas delivery tube 2 and gas sampling tube 4, in contrast to branched connector 16 that is illustrated as being disposed between tubes 6, 18, and 22 (see FIGS. 1A and 1D). Gas delivery tubes 18', 22' can be sized to accommodate the alternate positioning of branched connector 16'. Tube 22' can be permanently or removably connected to bite block 100. For example, tube 22' can be positioned within recess 111 and/or gas delivery opening 110 of bite block 100 in a similar or identical manner as that described elsewhere herein with respect to tube 22.

Figure 9D:
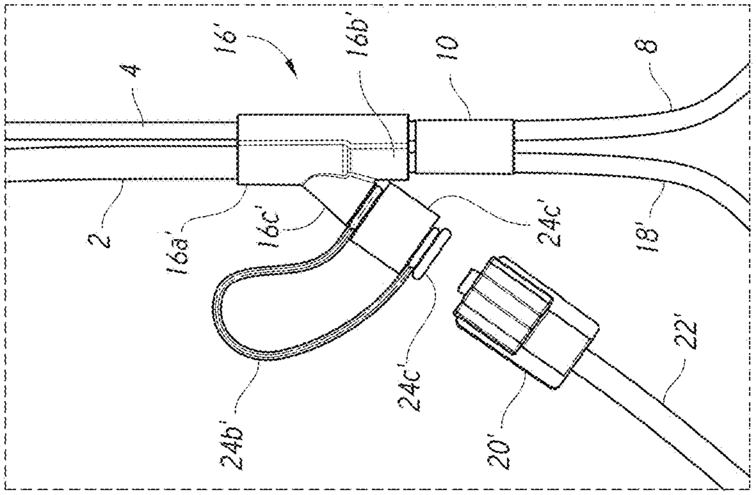
FIGS. 9B-9D illustrate enlarged views of a branched connector of the bite block assembly of FIG. 9A in accordance with aspects of this disclosure.
Figure 9C:
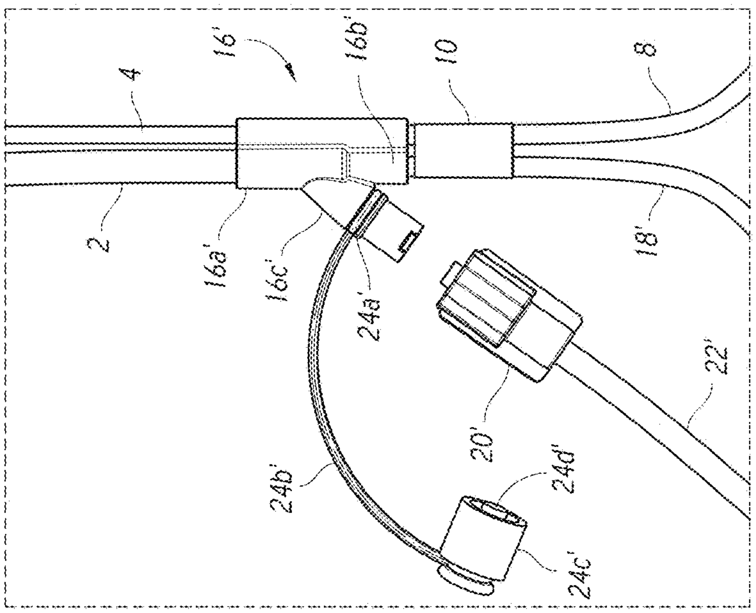
Figure 9B:
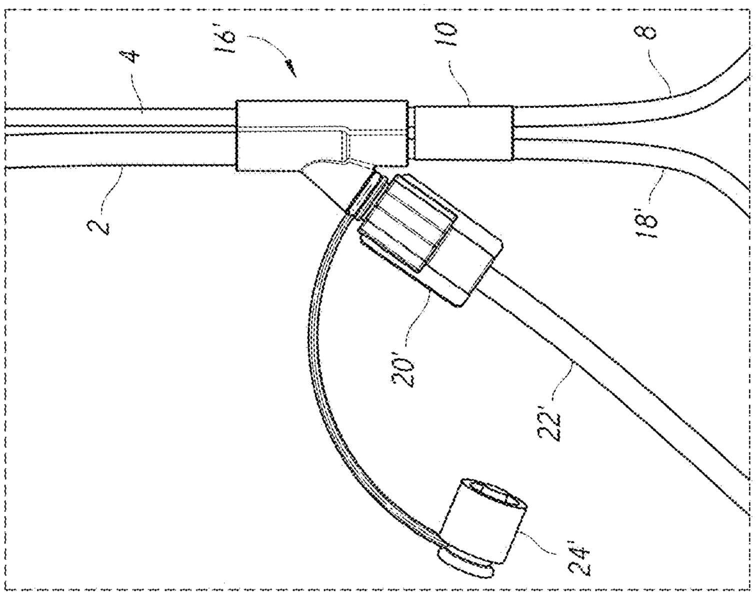

FIGS. 9B-9D illustrate enlarged views of branched connector 16', coupler 10, portions of tubes 2, 4, 8, 18', and a connector 20' coupled to an end of tube 22'. Branched connector 16' can include a first branch 16*a*', a second branch 16*b*', and a third branch 16*c*'. First branch 16*a*', a second branch 16*b*', and a third branch 16*c*' can be similar or identical to first branch 16*a*, a second branch 16*b*, and a third branch 16*c* in some, or many respects. Branch 16*a*' can be permanently or removably connected to tube 2 and/or branch 16*b*' can be permanently or removably connected to tube 18' and/or tube 8. In some implementations, coupler 10 is included in nasal cannula assembly 15'. However, in alternative implementations, coupler 10 is not included. Branch 16*c*' can be configured to removably connect to gas delivery tube 22', for example, via connector 20' secured to an end of tube 22'. Connector 20' can be configured to secure to branch 16*c*' via a snap fit engagement. Alternatively, connector 20' can secure to branch 16*c*' via a threaded engagement. Connection between connector 20' and branch 16*c*' can facilitate fluid communication between tube 22' and tube 2, thereby allowing gases (for example, oxygen) to be delivered by tube 2 and branch 16*c*' to tube 22' (and to gas delivery channel 110 of bite block 100). Branch 16*b*' can facilitate fluid communication between tube 18' and tube 2. Branch 16*a*' can facilitate fluid communication between tube 8 and tube 4. Branched connector 16' can include an interior defined by interiors of branches 16*a*', 16*b*', 16*c*'. Branched connector 16' can include a main body from which branch 16*c*' extends (for example, at an angle), and such main portion can be bifurcated into a first portion that is in fluid communication with tubes 2, 18' and a second portion that is in fluid communication with tubes 4, 8. Such first and second portions of such main body can be separated from one another.

As shown in FIGS. 9B-9D, a cap 24' can be secured to branched connector 16'. FIG. 9B shows tube 22' and connector 20' attached to branch 16*c*', FIG. 6C illustrates tube 22' and connector 20 unattached to branch 16*c*', and FIG. 9D illustrates tube 22' and connector 20 unattached to branch 16*c*' and cap 24' in a closed state. Cap 24' can be secured to a portion of branch 16*c*' to enable a fluid flow path through branch 16*c*' to be closed when connector 20' and tube 22' are not connected to branch 16*c*'. Cap 24' can include a base 24*a*' secured to (for example, around) branch 16*c*', a lid 24*c*' (which may also be referred to as a "closure portion"), and a strap 24*b*' positioned between and connecting base 24*a*' and lid 24*c*'. Strap 24*b*' can be flexible to allow lid 24*c*' to move relative to base 24*a*'. In some implementations, cap 24' (for example, base 24*a*') is permanently secured to branched connector 16' (for example, to branch 16*c*'). FIG. 9C illustrates cap 24' in an open position where branch 16*c*' is in fluid communication with the ambient environment when not connected with tube 22' (via connector 20'). In some implementations, a portion of connector 20' is inserted into branch 16*c*' when connected thereto. In some implementations, connector 20' is a male luer connector and branch 16*c*' includes a female luer connector. In some implementations, such luer connectors are threaded. FIG. 9D illustrates cap 24' in a closed position, where branch 16*c*' is not in fluid communication with the ambient environment. With reference to FIG. 9C, in some implementations, cap 24' includes a plug 24*d*' sized and/or shaped to fit and/or secure within branch 16*c*' (for example, an opening into an interior defined within branch 16*c*'). Such connection of plug 24*d*' within branch 16*c*' can be a friction fit arrangement, for example.

The bite block assemblies, bite blocks, nasal cannula assemblies, and/or components thereof disclosed herein can be utilized with monitoring devices that can provide capnography and/or anesthetic gas measurements. For example, the block assemblies, bite blocks, nasal cannula assemblies, and/or components thereof disclosed herein can be utilized with a gas analyzer such as ISA™ gas analyzers and/or Root® with ISA™ $CO_2$ Capnography which are commercially sold by Masimo Corporation. As another example, in some implementations, connector 14 (described above) can connect to a port in a monitoring device that provides capnography and/or anesthetic gas measurements based on the exhaled gas that is directed by the bite block 100 and/or nasal cannula assembly 15 to connector 14 by way of tube 8 and/or tube 4 (in addition to other structure of bite block 100 and/or nasal cannula assembly 15 as described in more detail elsewhere herein).

Additional Considerations and Terminology

Although this disclosure has been described in the context of certain examples, it will be understood by those skilled in the art that the present disclosure extends beyond the specifically disclosed examples to other alternative examples and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the examples may be made and still fall within the scope of the disclosure. Accordingly, it should be understood that various features and aspects of the disclosure can be combined with or substituted for one another in order to form varying modes of the disclosed.

Features, materials, characteristics, or groups described in conjunction with a particular aspect, or example are to be understood to be applicable to any other aspect, or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples of devices or systems. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that the actual steps taken in the processes illustrated and/or disclosed may differ from those shown in the figures. Depending on the system, certain of the steps described above may be removed, others may be added. Furthermore, the features and attributes of the specific examples disclosed above may be combined in different ways to form additional examples of systems, all of which fall within the scope of the present disclosure. Also, the separation of various system components in the implementations described above should not be understood as requiring such separation in all implementations, and it should be understood that the described components and systems can generally be integrated together in a single product or packaged into multiple products.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

While the above detailed description has shown, described, and pointed out novel features, it can be understood that various omissions, substitutions, and changes in the form and details of the devices or systems illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A bite block comprising:

a main body comprising a first surface and a second surface opposite the first surface, a first wing, a second wing, and an intermediate portion between the first and second wings, the first and second wings extending laterally away from the intermediate portion;

a mouthpiece extending outward from the second surface of the main body and configured to be positioned in a mouth of a subject when the bite block is in use, wherein the first and second wings of the main body are configured to be positioned on opposite sides of the subject's mouth and adjacent the subject's face when the mouthpiece is positioned in the subject's mouth, and wherein the mouthpiece comprises:

a main channel configured to receive an endoscopic tube; and a sampling channel configured to receive orally exhaled gases from the subject;

a gas delivery channel configured to direct gases into the subject's mouth when the bite block is in use, the gas delivery channel extending through the intermediate portion of the main body and through a portion of the main channel of the mouthpiece such that the gas delivery channel is in fluid communication with the main channel;

a gas delivery tube configured to deliver gases to the gas delivery channel, the gas delivery tube comprising a first end and a second end opposite the first end, wherein the second end is permanently secured within the gas delivery channel;

a tube clip located on a portion of the first wing of the main body, the tube clip comprising a first arm and a second arm, each of the first and second arms extending outward from the first wing and having free ends that are separated from one another by a gap, wherein the first and second arms are configured to secure a first portion of the gas delivery tube; and a recess extending along a portion of the first surface of the main body, the recess comprising a first end located at the gas delivery channel and a second end spaced away from the gas delivery channel, wherein the recess defines a longitudinal axis extending from the first end toward the second end and away from the gas delivery channel, and wherein the recess is configured to receive a second portion of the gas delivery tube outside of the gas delivery channel when the first portion of the gas delivery tube is secured between the first and second arms of the tube clip.

2. The bite block of claim 1, wherein an axis extending through a center of the gas delivery channel is transverse relative to an axis extending through a center of the main channel.

3. The bite block of claim 1, wherein the recess extends from the first end to the second end, and wherein the second end of the recess is located at a junction where the first wing and the intermediate portion of the main body meet.

4. The bite block of claim 1, wherein the recess extends from the gas delivery channel along the intermediate portion and toward the first wing.

5. The bite block of claim 4, wherein the recess extends from the gas delivery channel along the intermediate portion and toward the tube clip.

6. The bite block of claim 1, wherein the recess comprises a substantially semi-circular cross-section.

7. The bite block of claim 1, wherein the recess is configured to surround less than an entire cross-section of the second portion of the gas delivery tube.

8. The bite block of claim 1, wherein the recess is configured to surround less than about ¾ of a cross-section of the second portion of the gas delivery tube.

9. The bite block of claim 1, wherein a first portion of the gas delivery channel comprises a first cross-section and a second portion of the gas delivery channel comprises a second cross-section that is different than the first cross-section.

10. The bite block of claim 9, wherein a ledge is defined at a juncture of the first and second cross-sections of the gas delivery channel, and wherein the second end of the gas delivery tube abuts the ledge.

11. A bite block comprising:

a main body comprising a first surface and a second surface opposite the first surface;

a mouthpiece extending outward from the second surface of the main body and configured to be positioned in a mouth of a subject when the bite block is in use, and wherein the mouthpiece comprises:

a main channel configured to receive an endoscopic tube; and a sampling channel configured to receive orally exhaled gases from the subject;

a gas delivery channel configured to direct gases into the subject's mouth when the bite block is in use, the gas delivery channel extending through a portion of the main channel of the mouthpiece such that the gas delivery channel is in fluid communication with the main channel; and a recess extending along a portion of the first surface of the main body, the recess comprising a first end located at the gas delivery channel and a second end spaced away from the gas delivery channel, wherein the recess defines a longitudinal axis extending from the first end toward the second end and away from the gas delivery channel, and wherein the recess is configured to receive a portion of a gas delivery tube outside of the gas delivery channel.

12. The bite block of claim 11, wherein an axis extending through a center of the gas delivery channel is transverse relative to an axis extending through a center of the main channel.

13. The bite block of claim 11, wherein the main body comprises a first wing, a second wing, and an intermediate portion between the first and second wings, and wherein the second end of the recess is located at a junction where the first wing and the intermediate portion of the main body meet.

14. The bite block of claim 11, wherein the recess comprises a substantially semi-circular cross-section.

15. The bite block of claim 11, wherein the recess is configured to surround less than an entire cross-section of the portion of the gas delivery tube.

16. The bite block of claim 11, further comprising a tube clip located on a portion of the main body, the tube clip comprising a first arm and a second arm, each of the first and second arms extending outward from the portion of the main body and having free ends that are separated from one another by a gap, wherein the first and second arms are configured to secure the gas delivery tube.

17. The bite block of claim 11, wherein a first portion of the gas delivery channel comprises a first cross-section and a second portion of the gas delivery channel comprises a second cross-section that is different than the first cross-section.

18. The bite block of claim 17, further comprising said gas delivery tube, said gas delivery tube comprising a first end and a second end, wherein a ledge is defined at a juncture of the first and second cross-sections of the gas delivery channel, and wherein the second end of the gas delivery tube abuts the ledge.

19. The bite block of claim 1, wherein the second portion of the gas delivery tube extends along the recess outside of the gas delivery channel when the first portion of the gas delivery tube is secured between the first and second arms of the tube clip.

20. The bite block of claim 11, wherein the portion of the gas delivery tube is receivable laterally into the recess through an open side of the recess.

* * * * *